United States Patent
Davis et al.

(10) Patent No.: US 10,799,366 B2
(45) Date of Patent: Oct. 13, 2020

(54) INTERVERTEBRAL DEVICES AND RELATED METHODS

(71) Applicant: Spine View, Inc., San Jose, CA (US)

(72) Inventors: John Davis, Sunnyvale, CA (US); Al Mirel, Redwood City, CA (US); Mark Dias, San Jose, CA (US)

(73) Assignee: Expanding Innovations, Inc., Mountain View, CA (US)

( * ) Notice: Subject to any disclaimer, the term of this patent is extended or adjusted under 35 U.S.C. 154(b) by 94 days.

(21) Appl. No.: 14/120,379

(22) Filed: May 14, 2014

(65) Prior Publication Data

US 2015/0112437 A1   Apr. 23, 2015

Related U.S. Application Data

(60) Provisional application No. 61/955,757, filed on Mar. 19, 2014, provisional application No. 61/857,252, filed on Jul. 23, 2013, provisional application No. 61/822,919, filed on May 14, 2013.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3055* (2013.01); *A61F 2002/3093* (2013.01); *A61F 2002/30507* (2013.01); *A61F 2002/30537* (2013.01); *A61F 2002/30538* (2013.01); *A61F 2002/30556* (2013.01); *A61F 2002/30579* (2013.01); *A61F 2002/30772* (2013.01); *A61F 2002/4628* (2013.01)

(58) Field of Classification Search
CPC .... A61F 2/442–447; A61F 2002/30507; A61F 2002/30556; A61F 2002/30579; A61F 2002/30772; A61F 2002/3093; A61F 2002/4628
See application file for complete search history.

(56) References Cited

U.S. PATENT DOCUMENTS

| | | | |
|---|---|---|---|
| 4,863,476 A | * | 9/1989 | Shepperd .............. A61F 2/4455 623/17.15 |
| 5,860,973 A | | 1/1999 | Michelson |
| 6,562,074 B2 | | 5/2003 | Gerbec et al. |

(Continued)

FOREIGN PATENT DOCUMENTS

| WO | WO 2013/036707 | 3/2013 |
|---|---|---|
| WO | WO 2016/019230 | 2/2016 |

*Primary Examiner* — Tessa M Matthews
(74) *Attorney, Agent, or Firm* — Ross M. Carothers

(57) ABSTRACT

Intervertebral devices and systems, and methods of their use, are disclosed having configurations suitable for placement between two adjacent vertebrae, replacing the functionality of the disc therebetween. Intervertebral devices and systems contemplated herein are implantable devices intended for replacement of a vertebral disc, which may have deteriorated due to disease for example. The intervertebral devices and systems are configured to allow for ample placement of therapeutic agents therein, including bone growth enhancement material, which may lead to better fusion between adjacent vertebral bones. The intervertebral devices and systems are configured for use in minimally invasive procedures, if desired.

16 Claims, 35 Drawing Sheets

(56) References Cited

U.S. PATENT DOCUMENTS

| | | |
|---|---|---|
| 6,648,917 B2 | 11/2003 | Gerbec et al. |
| 6,852,129 B2 | 2/2005 | Gerbec et al. |
| 6,863,673 B2 | 3/2005 | Gerbec et al. |
| 6,986,772 B2 | 1/2006 | Michelson |
| 7,118,579 B2 | 10/2006 | Michelson |
| 7,204,853 B2 | 4/2007 | Gordon et al. |
| 7,235,082 B2 | 6/2007 | Bartish et al. |
| 7,316,714 B2 | 1/2008 | Gordon et al. |
| 7,655,027 B2 | 2/2010 | Michelson |
| 7,753,958 B2 | 7/2010 | Gordon et al. |
| 7,828,849 B2 | 11/2010 | Lim |
| 7,850,733 B2 | 12/2010 | Baynham |
| 7,909,869 B2 | 3/2011 | Gordon |
| 7,922,729 B2 | 4/2011 | Michelson |
| 7,967,867 B2 | 6/2011 | Barreiro et al. |
| 8,062,375 B2 | 11/2011 | Glerum et al. |
| 8,118,870 B2 | 2/2012 | Gordon et al. |
| 8,118,871 B2 | 2/2012 | Gorden et al. |
| 8,123,810 B2 | 2/2012 | Gorden et al. |
| 8,147,550 B2 | 4/2012 | Gorden et al. |
| 8,172,903 B2 | 5/2012 | Gordon et al. |
| 8,257,440 B2 | 9/2012 | Gordon et al. |
| 8,308,805 B2 | 11/2012 | Lynn et al. |
| 8,328,818 B1 | 12/2012 | Seifert et al. |
| 8,343,224 B2 | 1/2013 | Lynn et al. |
| 8,382,842 B2 | 2/2013 | Greenhalgh et al. |
| 8,398,713 B2 | 3/2013 | Weiman |
| 8,435,298 B2 | 5/2013 | Weiman |
| 8,444,692 B2 | 5/2013 | Michelson |
| 8,491,659 B2 | 7/2013 | Weiman |
| 8,496,664 B2 | 7/2013 | Michelson |
| 8,518,120 B2 | 8/2013 | Glerum et al. |
| 8,556,979 B2 | 10/2013 | Glerum et al. |
| 8,603,168 B2 | 12/2013 | Gordon et al. |
| 8,632,595 B2 | 1/2014 | Weiman |
| 8,647,386 B2 | 2/2014 | Gordon et al. |
| 8,679,183 B2 | 3/2014 | Glerum et al. |
| 8,685,098 B2 | 4/2014 | Glerum et al. |
| 8,709,086 B2 | 4/2014 | Glerum |
| 8,753,398 B2 | 6/2014 | Gordon et al. |
| 8,771,321 B2 | 7/2014 | Michelson |
| 8,894,712 B2 * | 11/2014 | Varela ............ A61F 2/447 623/17.16 |
| 8,940,048 B2 * | 1/2015 | Butler ............ A61F 2/442 623/17.15 |
| 9,155,628 B2 * | 10/2015 | Glerum ............ A61F 2/4455 |
| 9,271,777 B2 * | 3/2016 | Nichols ............ A61F 2/4611 |
| 9,358,123 B2 * | 6/2016 | McLuen ............ A61F 2/4455 |
| 9,402,739 B2 * | 8/2016 | Weiman ............ A61F 2/447 |
| 9,414,934 B2 * | 8/2016 | Cain ............ A61F 2/442 |
| 9,445,920 B2 * | 9/2016 | Baynham ............ A61F 2/447 |
| 9,463,099 B2 * | 10/2016 | Levy ............ A61F 2/442 |
| 9,717,601 B2 * | 8/2017 | Miller ............ A61F 2/4455 |
| 10,092,416 B2 * | 10/2018 | Davis ............ A61F 2/447 |
| 2004/0153065 A1 * | 8/2004 | Lim ............ A61F 2/4465 606/53 |
| 2006/0058880 A1 * | 3/2006 | Wysocki ............ A61F 2/4465 623/17.15 |
| 2008/0140207 A1 * | 6/2008 | Olmos ............ A61F 2/4455 623/17.11 |
| 2010/0204795 A1 | 8/2010 | Greenhalgh |
| 2010/0292796 A1 * | 11/2010 | Greenhalgh ........ A61B 17/8858 623/17.11 |
| 2011/0093074 A1 * | 4/2011 | Glerum ............ A61F 2/447 623/17.16 |
| 2011/0280453 A1 * | 11/2011 | Chen ............ G06T 7/75 382/113 |
| 2011/0282453 A1 * | 11/2011 | Greenhalgh ........ A61B 17/8858 623/17.16 |
| 2012/0150304 A1 | 6/2012 | Glerum |
| 2012/0150305 A1 | 6/2012 | Glerum |
| 2012/0158146 A1 | 6/2012 | Glerum |
| 2012/0158147 A1 | 6/2012 | Glerum et al. |
| 2012/0158148 A1 | 6/2012 | Glerum |
| 2013/0158663 A1 * | 6/2013 | Miller ............ A61F 2/4455 623/17.16 |
| 2013/0158669 A1 * | 6/2013 | Sungarian ............ A61F 2/442 623/17.16 |
| 2013/0211525 A1 * | 8/2013 | McLuen ............ A61F 2/4455 623/17.16 |
| 2014/0039622 A1 | 2/2014 | Glerum et al. |
| 2014/0052254 A1 | 2/2014 | Glerum et al. |
| 2014/0058516 A1 | 2/2014 | Glerum et al. |
| 2014/0058519 A1 | 2/2014 | Glerum et al. |
| 2014/0094916 A1 | 4/2014 | Glerum et al. |
| 2014/0121774 A1 | 5/2014 | Glerum et al. |
| 2014/0128977 A1 | 5/2014 | Glerum et al. |
| 2014/0180421 A1 * | 6/2014 | Glerum ............ A61F 2/4611 623/17.16 |

* cited by examiner

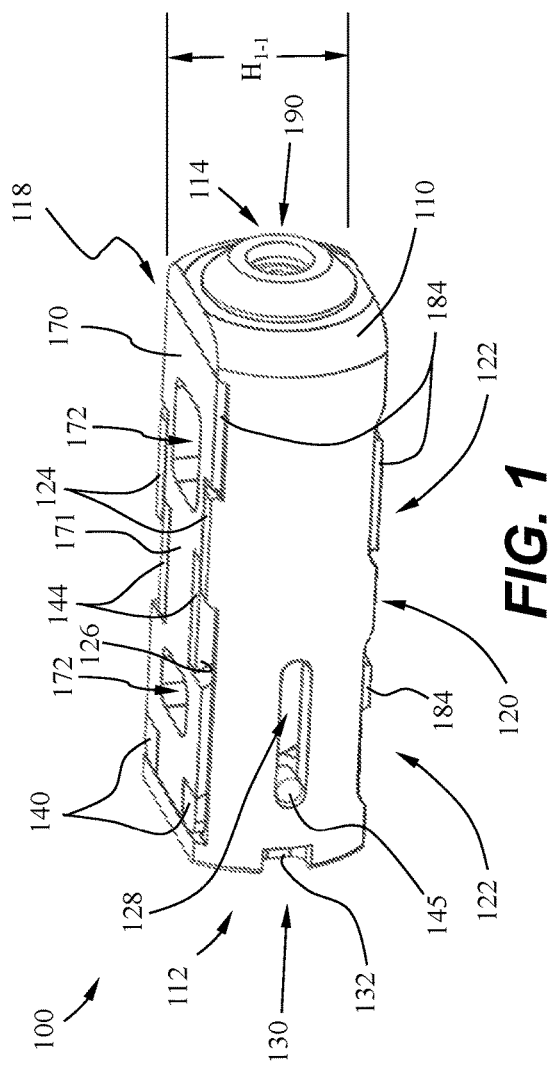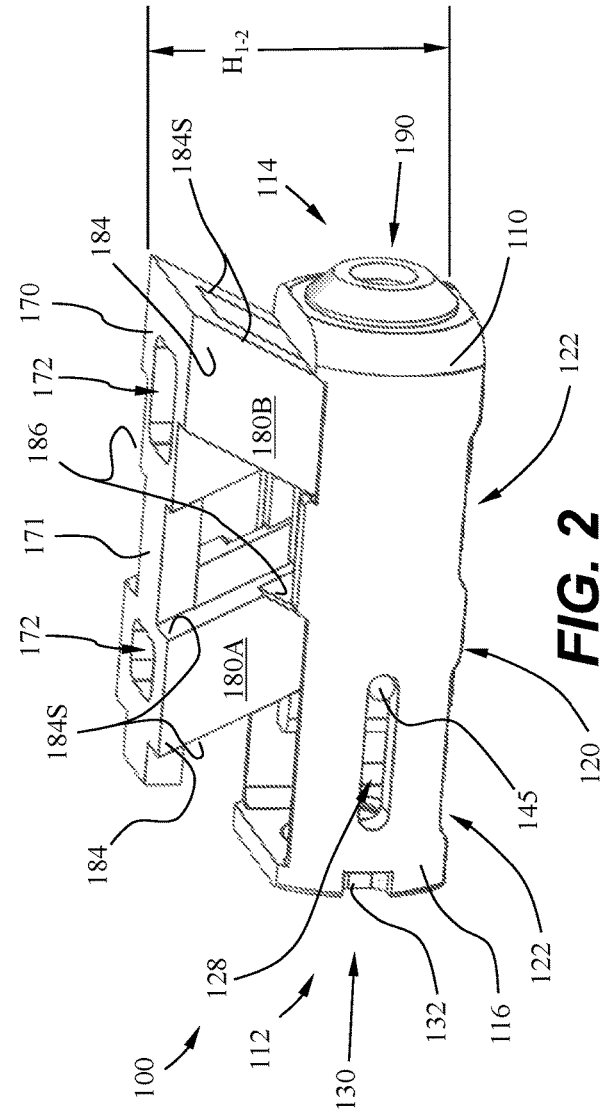

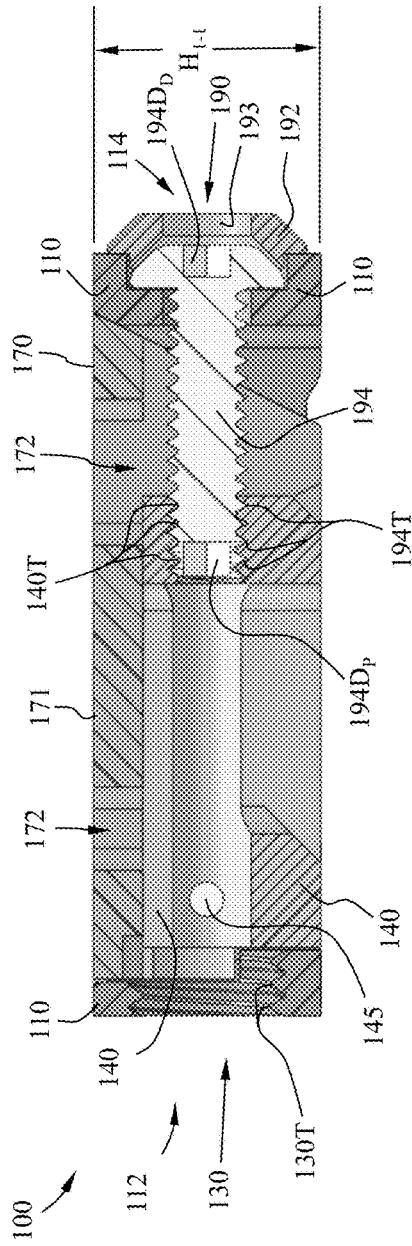
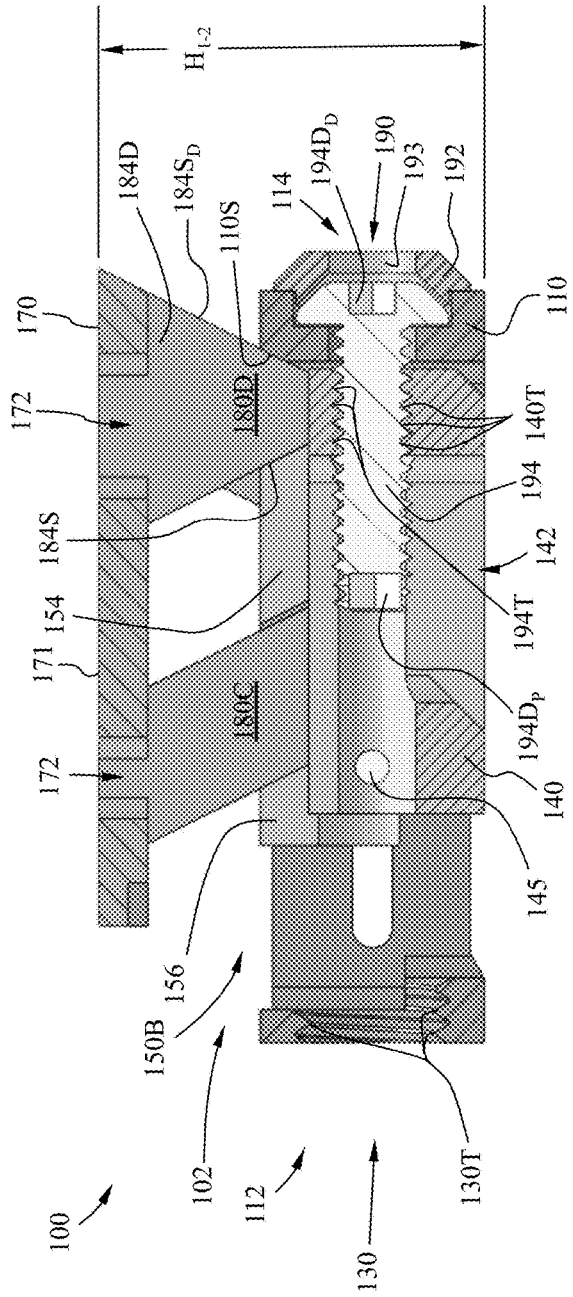
FIG. 3
FIG. 4

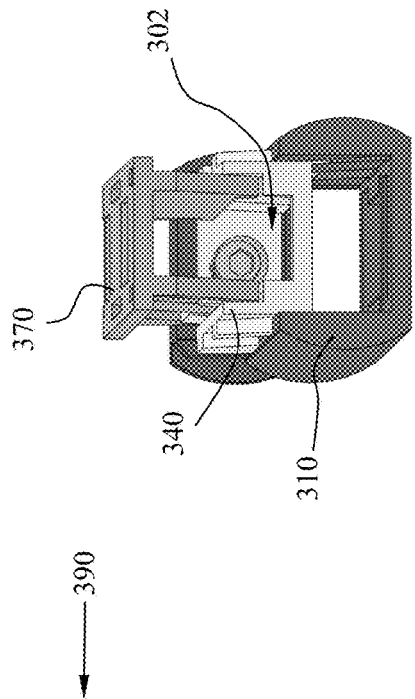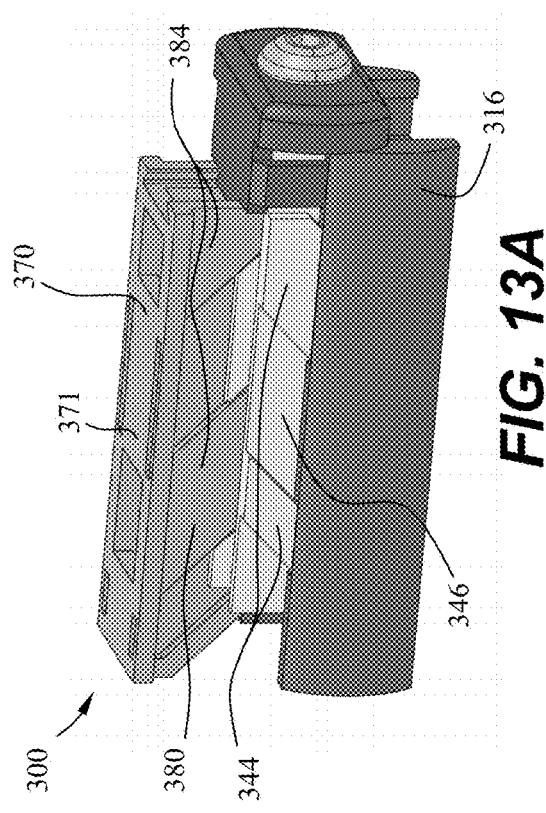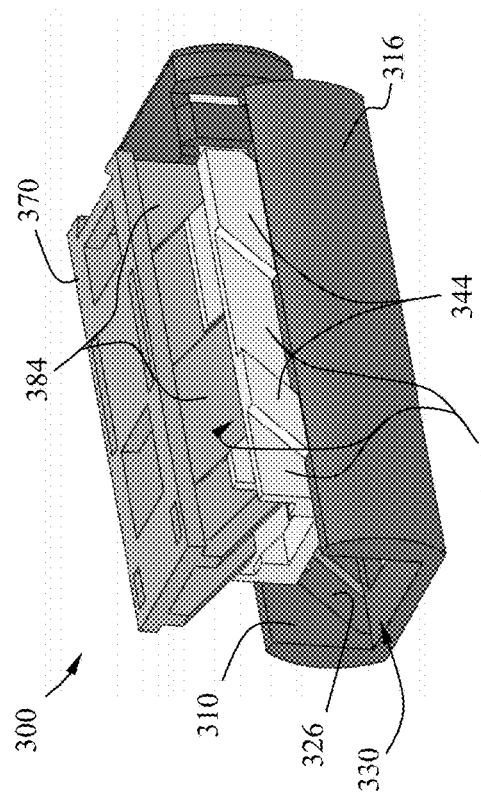

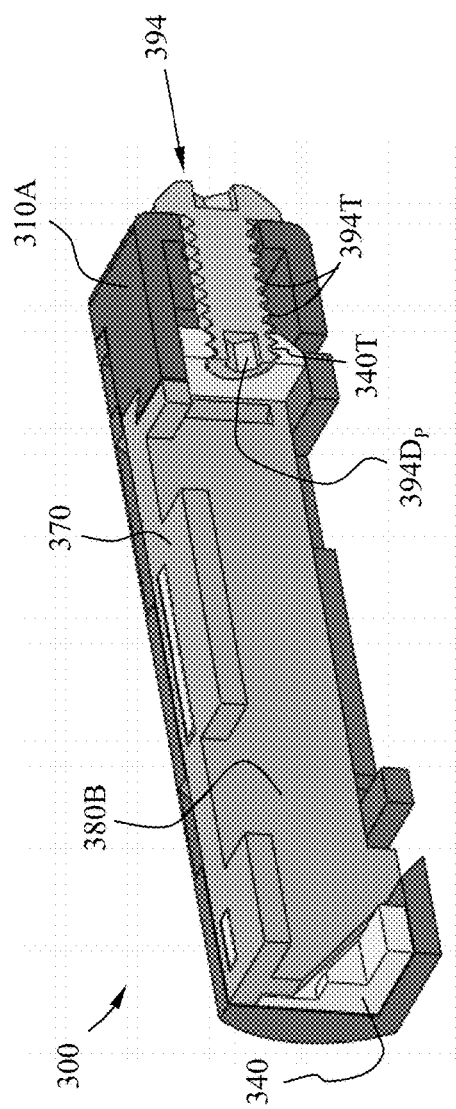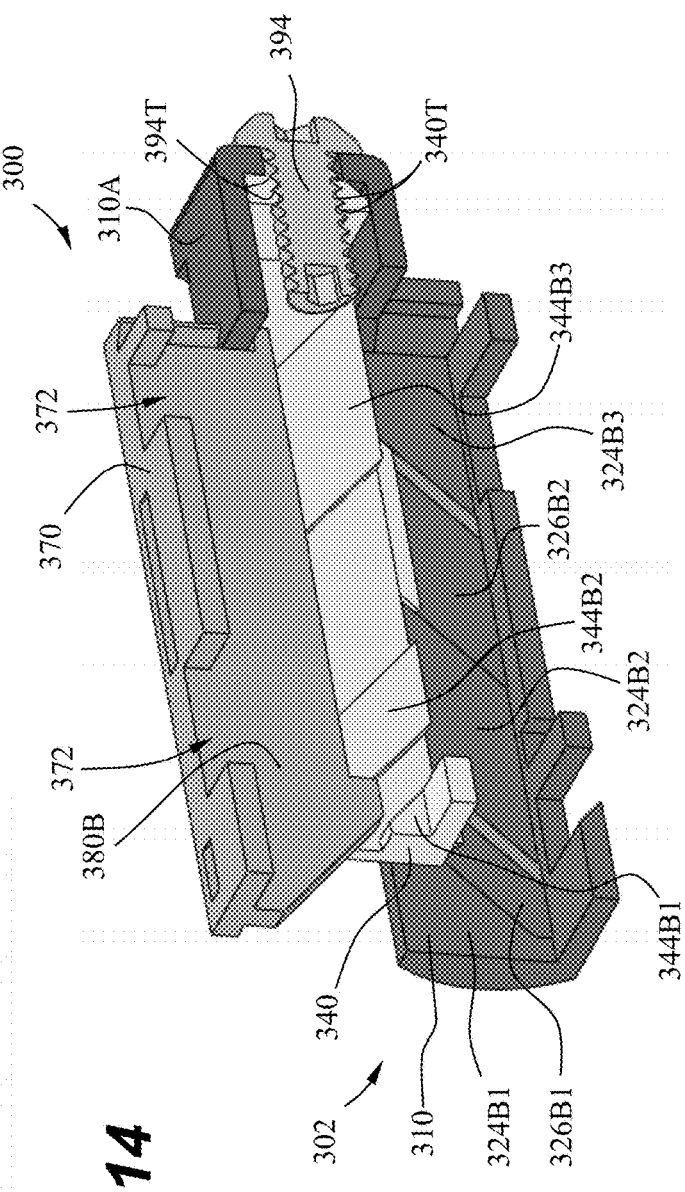

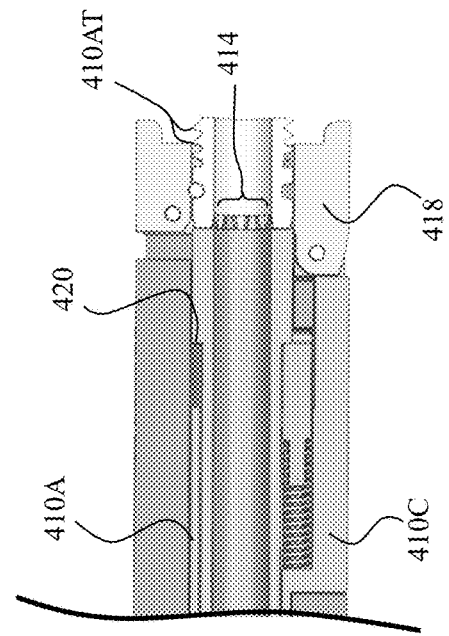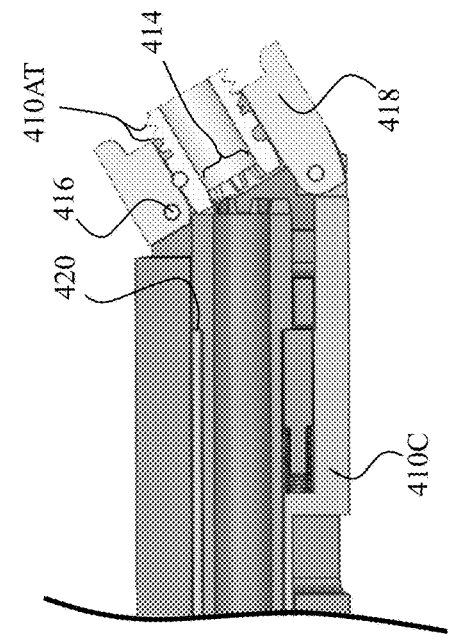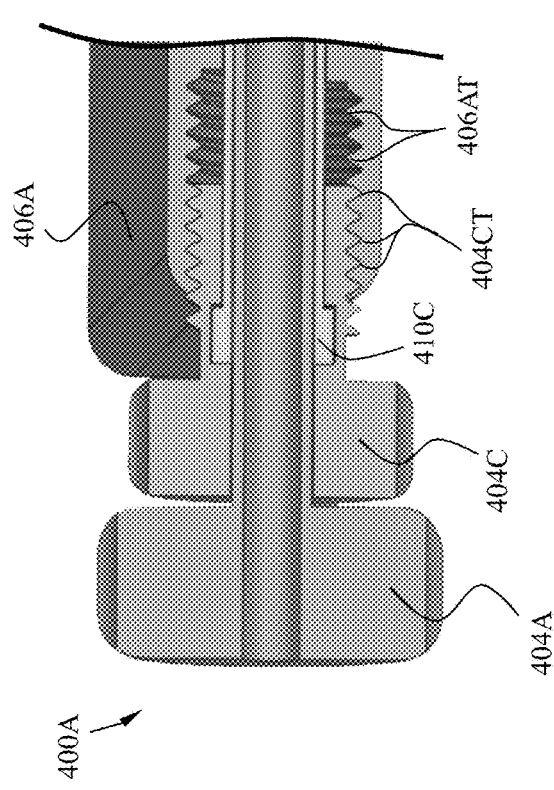
FIG. 22
FIG. 23

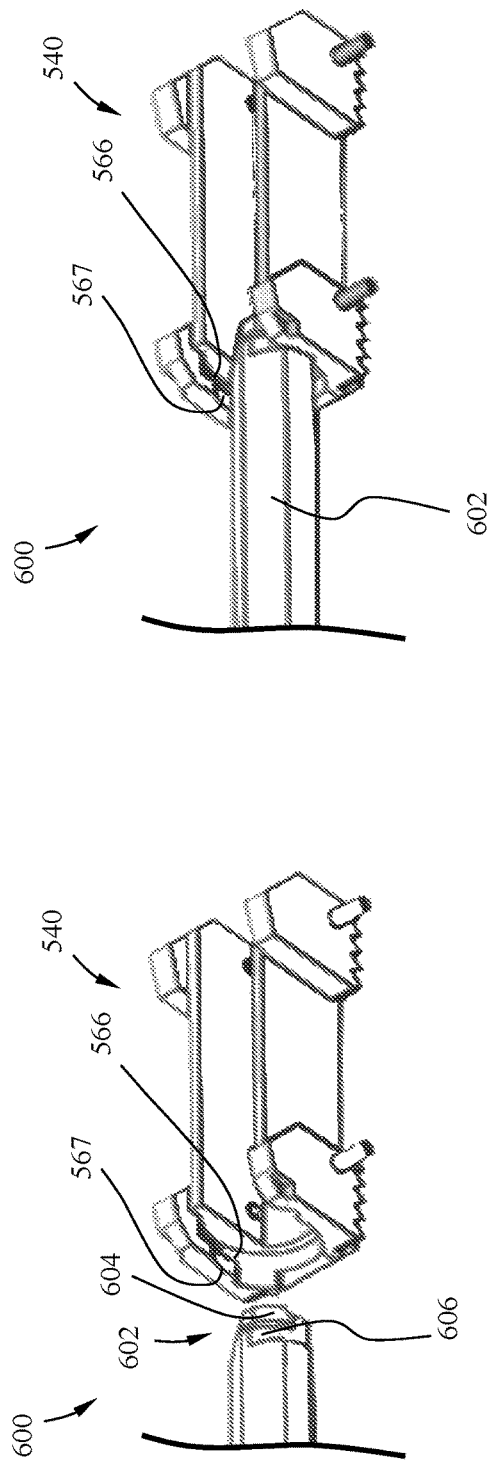
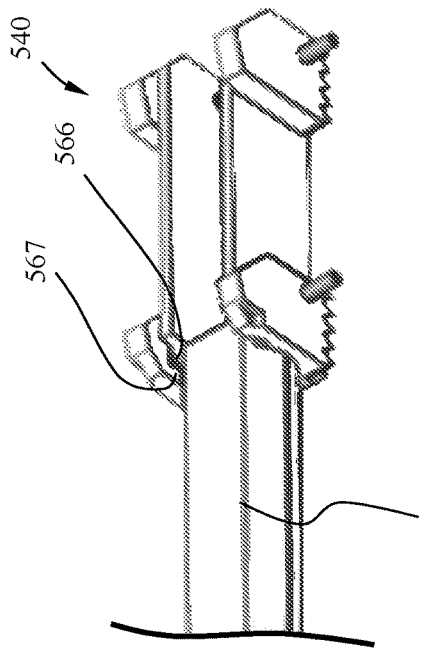
FIG. 30A
FIG. 30B
FIG. 30C

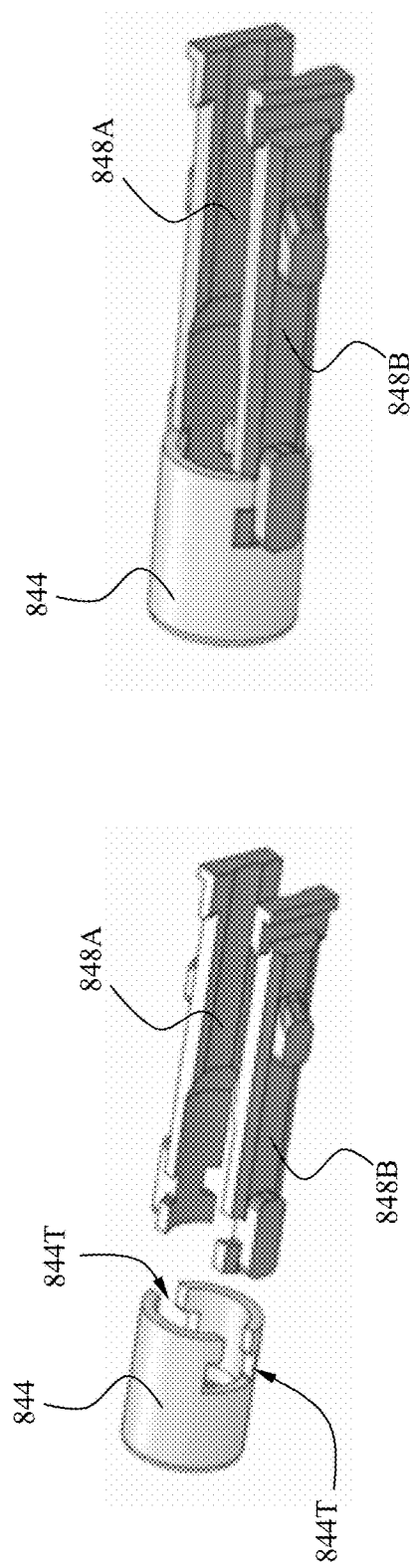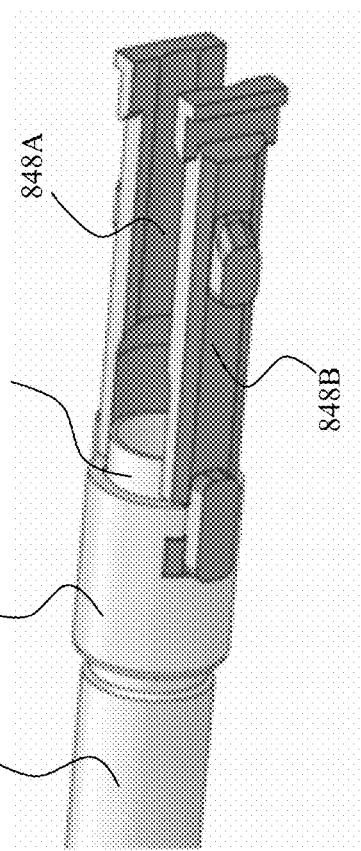
FIG. 42A
FIG. 42B
FIG. 42C

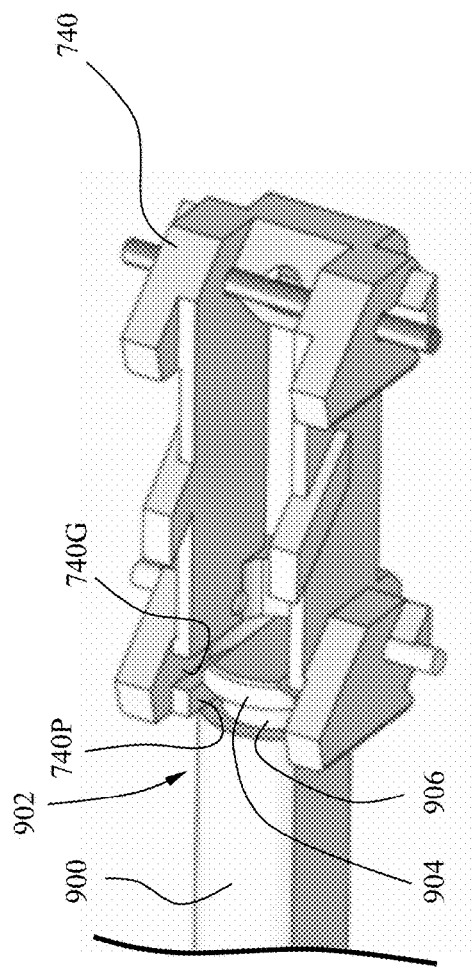
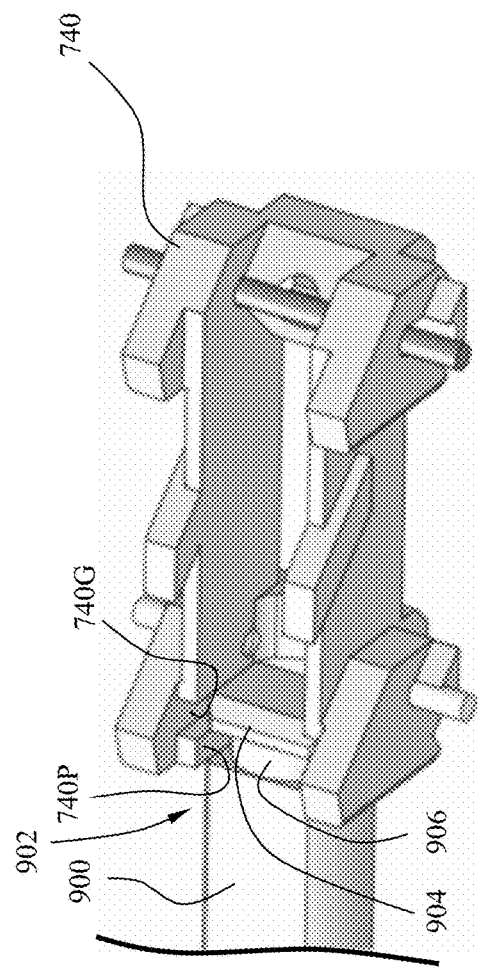
FIG. 46A
FIG. 46B

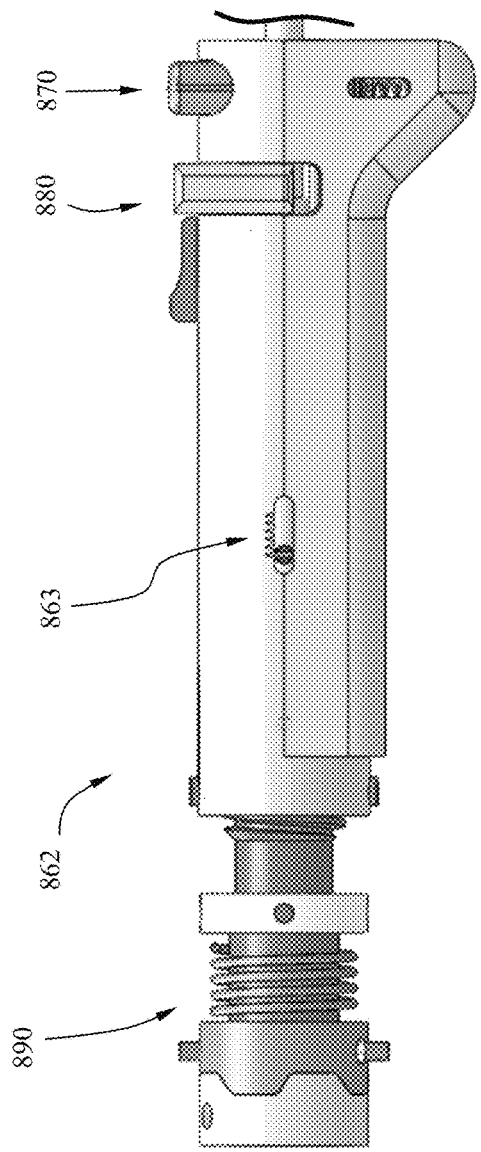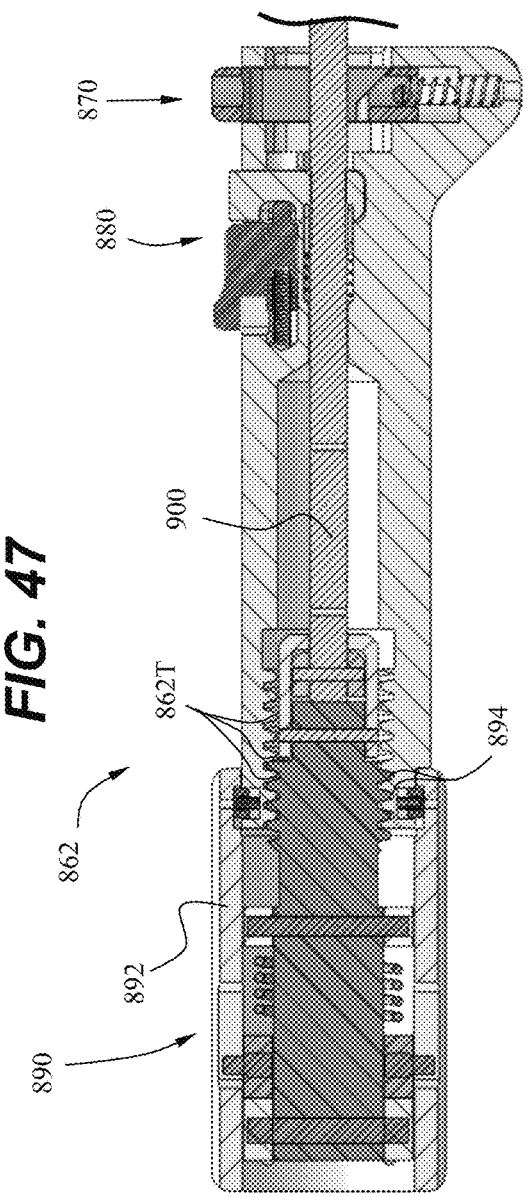
FIG. 47
FIG. 48

INTERVERTEBRAL DEVICES AND RELATED METHODS

This application claims priority to U.S. Provisional Application Ser. No. 61/822,919, entitled "Intervertebral Devices and Related Methods," filed May 14, 2013, U.S. Provisional Application Ser. No. 61/857,252, entitled "Intervertebral Devices and Related Methods, Filed Jul. 23, 2013, and U.S. Provisional Application Ser. No. 61/955,757, entitled "Intervertebral Devices and Related Methods," filed Mar. 19, 2014, which applications are incorporated herein by reference in their entirety.

BACKGROUND

Field of this Disclosure

This disclosure relates generally to medical devices, and more particularly, to medical devices utilized for spinal procedures.

Description of the Related Art

Degenerative disc diseases are common disorders that can impact all or a portion of a vertebral disc, a cushion-like structure located between the vertebral bodies of the spine. Degenerative disc diseases may lead, for example, to a disc herniation where the vertebral disc bulges out or extrudes beyond the usual margins of the disc and the spine. Disc herniation, in particular, is believed to be the result of excessive loading on the disc in combination with weakening of the annulus due to such factors as aging and genetics. Such degenerative disc diseases are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation, or other degenerative disc diseases, is often sought through conservative therapy, which includes positional therapy (e.g. sitting or bending forward to reduce pressure on the spine), physical therapy, and drug therapy to reduce pain and inflammation. When conservative therapy fails to resolve a patient's symptoms, surgery may be considered to treat the structural source of the symptoms. When surgery fails to resolve a patient's symptoms, more drastic measures may include disc replacement surgery or vertebral fusion.

There are numerous implantable devices that have been developed for disc replacement and vertebral fusion. Such implantable devices, also referred to as cage systems, may be deployed to replace the vertebral disc and fuse the adjacent vertebrae, relieving pain and providing increased mobility to the patient. However, known implantable devices and methodologies have drawbacks. For example, many of the implantable devices currently available do not allow for an ample amount of materials to encourage bone growth to be positioned within and around the devices and adjacent vertebral bones. Such gone growth materials allow for a higher level of fusion of the adjacent vertebrae, providing increase stabilization and minimize the likelihood of further issues in the future. Also, many implantable devices are large structures that are not easily utilized in a minimally invasive procedure. Rather, they may require surgical procedures allowing greater access, which subjects the patient to higher risks of disease and prolonged infection.

There is a need for implantable devices intended for replacement of a vertebral disc, which allow for ample placement of bone growth material that may lead to better fusion between adjacent vertebral bones. There is a further need for such implantable devices to be provided during minimally invasive procedures, reducing the risk of infection and allowing for quicker healing of the patient.

BRIEF SUMMARY

Consistent with the present disclosure, an expandable intervertebral device may comprise a base including a bottom surface configured to interface with a first biological tissue, a first body portion slidably attached to the base and configured to move in at least a first direction with respect to the base, the first body portion including a first engaging element, and a second body portion slidably attached to the base and configured to move in at least a second direction with respect to the base. The second body portion may include a top surface configured to interface with a second biological tissue. The base may include a second engaging element such that the second engaging element couples to the first engaging element. In certain embodiments, the first and second engaging elements are configured such that the coupling of the first and second engaging elements prevents movement of the second body portion in a third direction with respect to the base when a compression force is applied between the top surface of the second body portion and the bottom surface of the base. In other embodiments, the third direction is substantially opposite to the first direction, while in still other embodiments, the third direction is substantially opposite to the first direction.

In yet other embodiments, the first body portion may include a first sloped surface and the second body portion may include a second sloped surface. The first sloped surface may be configured to slidably couple with the second sloped surface, such that movement of the first body portion in the first direction results in movement of the second body portion in the second direction. The first sloped surface of the first body portion may form a first acute angle with respect to a longitudinal axis of the base, and the second sloped surface of the second body portion may form a second acute with respect to the longitudinal axis of the base. In some embodiments, the first acute angle is substantially equal to the second acute angle, while in other embodiments the first acute angle is different than the second acute angle. In still other embodiments, the first sloped surface of the first body portion may form a first acute angle with respect to a longitudinal axis of the base, and the second sloped surface of the second body portion may form a second acute with respect to the longitudinal axis of the base. Movement of the second body portion relative to the first body portion may define a movement rate, the first and second acute angles may be selected to provide the movement rate.

In certain embodiments, the first body portion may be configured to be removably attached to a translating member, where operation of the translating member results in movement of the first body portion in the first direction, generally along a longitudinal axis of the base. In some embodiments, the base includes a longitudinal axis, and the first direction is substantially parallel to the longitudinal axis of the base, while in other embodiments, the base includes a longitudinal axis, the second direction being substantially perpendicular to the longitudinal axis of the base. In other embodiments, the first direction and the second direction are substantially perpendicular.

In still other embodiments, the base includes first and second ends, and a longitudinal axis extending from the first end to the second end, and each of a plurality of positions of the first body portion along the longitudinal axis of the base corresponding to a respective one of a plurality of positions of the second body portion. Each of the plurality of positions of the first body portion may correspond to a respective one of a plurality of heights of the intervertebral device.

In yet other embodiments, the first direction is in a direction toward a distal end of the device along a longitudinal axis of the base, while in other embodiments the first direction is in a direction toward a proximal end of the device along a longitudinal axis of the base.

In another aspect, a method includes providing an intervertebral device having a base, a first body portion, and a second body portion, the first body portion configured to move in at least a first direction with respect to the base and the second body portion configured to move in at least a second direction with respect to the base, the first body portion including a first engaging element and the base portion including a second engaging element;

moving the first body portion in the first direction, the second body portion moving in the second direction in response to movement of the first body portion, the first engaging element of the first body portion couples to the second engaging element of the base, the coupling of the first and second engaging elements preventing movement of the second body portion in a third direction.

In certain embodiments, the base, and the first and second body portions form a void, movement of the first body portion in the first direction results in increasing an area of the void. The method may include deploying one or more therapeutic agents within the void, the therapeutic agents including a substance to encourage bone growth, for example. A central axis of each of the base, and first and second body portions may pass through the void.

In other embodiments, moving the first element in the first direction results in adjusting the height of the intervertebral device. Adjusting the height may include expanding and contracting the intervertebral device.

In yet other embodiments, the first direction is in a direction toward a distal end of the device along a longitudinal axis of the base, while in other embodiments, the first direction is in a direction toward a proximal end of the device along a longitudinal axis of the base.

It is to be understood that both the foregoing general description and the following detailed description are exemplary and explanatory only and are not restrictive of the any embodiments, as claimed. Other objects, features and advantages of the embodiments disclosed or contemplated herein will be apparent from the drawings, and from the detailed description that follows below.

BRIEF DESCRIPTION OF THE DRAWINGS

Reference will be made to embodiments of the disclosure, examples of which may be illustrated in the accompanying figures. These figures are intended to be illustrative, not limiting. Although certain aspects of the embodiments are generally described in the context of these embodiments, it should be understood that it is not intended to limit the scope to these particular embodiments. In the drawings:

FIG. 1 is a perspective view of an intervertebral device in a first configuration.

FIG. 2 is a perspective view of the intervertebral device of FIG. 1 in a second configuration.

FIG. 3 is a partial section view of the intervertebral device of FIG. 1.

FIG. 4 is another partial section view of the intervertebral device of FIG. 2.

FIGS. 13A-13C are perspective views of the intervertebral device of FIG. 12 in a second configuration.

FIG. 14 is a partial section view of the intervertebral device of FIG. 12.

FIG. 15 is a partial section view of the intervertebral device of FIGS. 13A-13C.

FIG. 22 is a partial section view of a portion of the exemplary delivery device of FIG. 21.

FIG. 23 is another partial section view of a portion of the exemplary delivery device of FIG. 21.

FIGS. 30A-30C are perspective views of an exemplary delivery device interfacing with a portion of an exemplary intervertebral device.

FIGS. 42A-C are perspective views of certain elements of the portion of the exemplary delivery device of FIG. 37.

FIGS. 46A-46B are perspective views of a portion of the element FIG. 44.

FIG. 47 is a partial cut view of a portion of the element of FIG. 44.

FIG. 48 is a partial section view of a portion of the element of FIG. 44.

DETAILED DESCRIPTION

Figure 5:
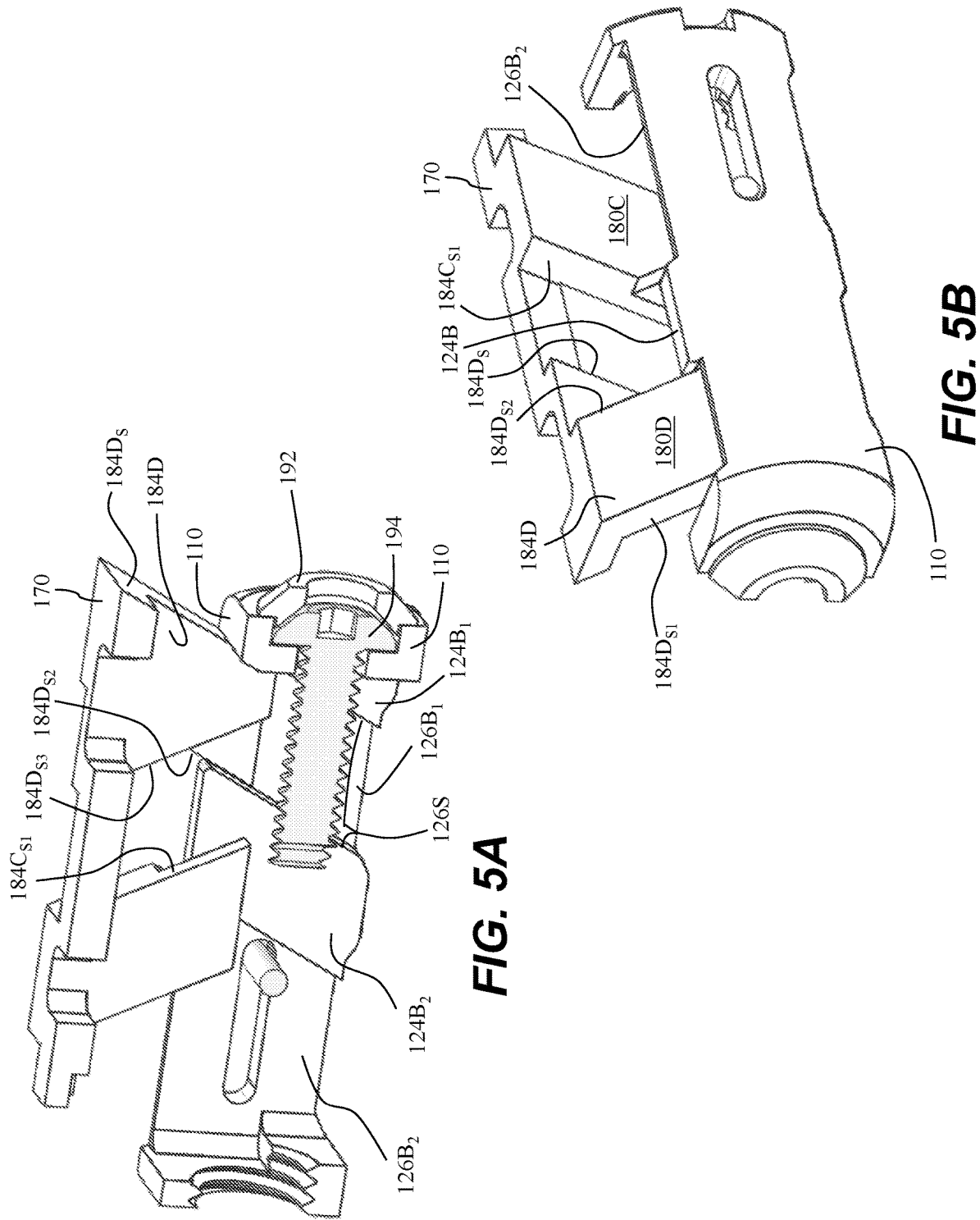
FIG. 5A is a partial section view of a portion of the intervertebral device of FIG. 2.
FIG. 5B is another partial section view of a portion of the intervertebral device of FIG. 2.

Intervertebral devices and systems, and methods of their use, are disclosed having configurations suitable for placement between two adjacent vertebrae, replacing the functionality of the disc therebetween. Intervertebral devices and systems contemplated herein are implantable devices intended for replacement of a vertebral disc, which may have deteriorated due to disease for example. The intervertebral devices and systems are configured to allow for ample placement of therapeutic agents therein, including bone growth enhancement material, which may lead to better fusion between adjacent vertebral bones. The intervertebral devices and systems are configured for use in minimally invasive procedures, if desired.

The following description is set forth for the purpose of explanation in order to provide an understanding of the various embodiments of the present disclosure. However, it is apparent that one skilled in the art will recognize that embodiments of the present disclosure may be incorporated into a number of different systems and devices.

The embodiments of the present disclosure may include certain aspects each of which may be present in one or more medical devices or systems thereof. Structures and devices shown below in cross-section or in block diagram are not necessarily to scale and are illustrative of exemplary embodiments. Furthermore, the illustrated exemplary embodiments disclosed or contemplated herein may include more or less structures than depicted and are not intended to be limited to the specific depicted structures. While various portions of the present disclosure are described relative to specific structures or processes with respect to a medical device or system using specific labels, such as "locked" or "therapeutic agents", these labels are not meant to be limiting.

The expandable intervertebral devices described herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding). The intervertebral devices herein may be sized for minimally invasive procedures having operating lumens at about 12 mm or less. For illustration purposes only, any expandable intervertebral device described or contemplated herein may have a height in the range from about 6 mm to about 16 mm, and a length in the range of from about 20 to about 40 mm, and a width in the range of from about 8 mm to about 16 mm. The intervertebral devices described or contemplated herein may be positioned between adjacent vertebrae through any suitable procedure, such as through a posterior lumbar interbody approach or through a transforaminal lumbar interbody approach, for example.

Reference will now be made in detail to the present exemplary embodiments, which are illustrated in the accompanying drawings.

Turning to FIGS. 1 and 2, a perspective view of an exemplary intervertebral device 100 includes a first element or base element 110, a second or sliding element 140, a third or elevating element 170, and a drive mechanism 190. As will be better understood in the discussion below, the elements 110, 140, 170 cooperate such that the intervertebral device 100 geometric height, H, may have a minimum, collapsed configuration, as generally depicted in FIG. 1, or a maximum, expanded configuration, as generally depicted in FIG. 2, or any height therebetween, as discussed in greater detail below. As will be better understood in light of the discussion below, the elements 110, 140, 170 include protrusions and depressions that cooperate to allow coordinated movement of each of the element 110, 140, 170 with respect to each other. For example, as the second element 140 translates from a proximal position to a distal position within the first element 110, protrusions and depressions of the elements 110, 140, 170 cooperate resulting in the elevation of the third element 170 with respect to the first and second elements 110, 140.

The first element 110 is configured to provide a base or outer structure for the intervertebral device 100, retaining the remaining elements 140, 170 therein. The first element 110 includes a first or proximal end 112 and a second or distal end 114 and two side portions, a first side portion 116 and an opposing side portion 118. A bottom portion 120 of the first element 110 may include one or more openings 122 to allow for therapeutic materials, such as bone growth enhancing materials, to pass therethrough. As used herein, the term "therapeutic materials" or therapeutic agents" may include any substance, including bone growth materials or drug eluding materials for example, or a product or medical device including or deploying such substances, intended for use in the medical diagnosis, cure, treatment, or prevention of disease.

Proximal end 112 of the first element 110 may include an opening 130 for passing a portion of one or more tools utilized for expanding, contracting, or locking the intervertebral device 100 in a specific configuration, as is discussed in greater detail below with reference to FIGS. 3 and 4. For example, the intervertebral device 100 may be expanded from a first position or configuration, having a height of $H_{1-1}$, as depicted in FIG. 1, to a second position or configuration, having a height of $H_{1-2}$, as depicted in FIG. 2, or any suitable height therebetween, and locked in any such configuration or at any such height. As used herein, the term "lock", "locked" or "locking" used in conjunction with the intervertebral device 100, or any other intervertebral device described or contemplated herein, shall mean to substantially maintain the position of each of the main elements, such as elements 110, 140, 170, with respect to each other. A void or space 102 is defined by the elements 110, 140, 170 when the intervertebral device 100 takes on a collapsed configured, as depicted in FIG. 1, and the void or space 102 increases when the intervertebral device 100 takes on an expanded configuration, as depicted in FIG. 2. Therapeutic Agents may then be deployed through opening 120, or other suitable opening, to fill the void 102 and expand out of the intervertebral device 100 to engage surrounding tissue, e.g. tissue of the vertebra.

The proximal end 112 of the first element 110 may also include structures, such as a threaded structure 130T, as better shown in FIGS. 3 and 4, and recesses 132, which may allow for an attachment point of one or more delivery systems, as described in greater detail below with respect to FIG. 17. Such attachment point may also form the basis for at least initially positioning the intervertebral device 100, for example between two adjacent vertebrae of a spine. In other embodiments, the delivery system utilized may include tubular members through which therapeutic materials, including bone growth enhancing materials, may be introduced, for example, to internal voids or spaces within the intervertebral device 100, and exiting through the one or more openings 120 of the element 110, or similar openings of the remaining elements 140, 170. In this way, such materials may contact surrounding tissues, such as tissues of the vertebrae.

The internal sidewalls of side portions 116, 118 of the first element 110 may include one or more protrusions 124 and one or more depressions 126, as better viewed with respect to FIG. 5A. These protrusions 124 and depressions 126 include surfaces that interface with one or more surfaces of protrusions and depressions of the other elements 140, 170 resulting in coordinated movement.

The second element 140 is slidably interfaced to the first element 110 such that the second element 140 at least translates horizontally with respect to the first element 110. Second element 140 may include a positioning structure or pin 145 that is coupled to the second element 140. The pin 145 may be configured or adapted to move within a channel or slot 128 provided in the first element 110 to ensure that the second element 140 moves in a specific direction with respect to the element 110. Accordingly, slot 128 and associated structure or pin 145 may be configured to form any desirable angle with respect to a longitudinal centerline of element 110. As depicted, slot 128 is substantially parallel to a longitudinal line of element 110 and, therefore, the element 130 moves in a direction substantially perpendicular to element 110. The second element 140 may also include one or more openings 142 that are in fluid communication with openings of one or more other elements 110, 170, such as openings 122 of the first element 110, to allow for passage of therapeutic agents therethrough.

The third element 170 includes a top surface 171 having one or more openings 172 that are in fluid communication with void 102. The top surface may include other structures to enable or encourage contact and retention with respect to a bodily tissue, such as tissue of a vertebra. The third element 170 may include one or more side members 180, each having one or more protrusions 184 and one or more depressions 186 and corresponding surfaces that cooperate with surfaces of the first and second elements 110, 140 to allow for cooperative movement.

Turning to FIGS. 3 and 4, which depict the intervertebral device 100 in cross-section down a central longitudinal axis, drive mechanism 190 includes a retaining cap 192 and drive member 194. The drive member 194 may include drive points 194D configured to receive a driver for rotational control of the member 194. The retaining cap 192 may be fixedly attached to the first element 100 to retain the drive member 194 within the intervertebral device 100 and provide a surface force to allow for the translation of the second element 140. For example, as depicted, the drive member 194 may include a proximal drive point $194D_P$ located closer to proximal end 112 of the first element 110, and a distal drive point $194D_D$ located closer to distal end 112 of the first element 110. As is discussed in greater detail below, a driver may enter through opening 130, pass through void 102, and engage the proximal drive point $194D_P$, rotation of the driver resulting in corresponding rotation of the driver member 194, for example. The retaining cap 192 may include an opening 193 for driver access to the distal drive point $194D_D$, if desired.

The driver member 194 includes a helical threaded portion 194T configured or adapted to interface with a helical threaded portion 140T of the second element 140. Accordingly, rotation of the drive member 194 results in axial movement of the second member 140. More specifically, if the drive member 194 is rotated in a first direction, the second element 140 will move in a distal direction, toward distal end 114 of the first element 110, and if the drive member 194 is rotated in a second opposing direction, the second element 140 will move in a proximal direction, toward proximal end 112 of the first element 110. Since the threads 194T, 140T are continuous, the second element 140 may be positioned at any point along a longitudinal axis of the first element 110, each point along the longitudinal axis corresponding to a respective height of the third element 170.

With specific reference to FIG. 4, depicting the intervertebral device 100 in cross-section through a central geometric plane, the second element 140 includes side members 150A (not shown) and 150B, collectively referred to as side members 150. As depicted, side member 150B includes one or more protrusions 154 and one or more depressions 156 that interface with other structures of the third element 170 such that when the second element 140 translates distally the third element 170 moves at least vertically, increasing an overall height of the intervertebral device 100. For example, protrusion 154 includes a sloped surface $154_{S1}$ that interfaces with an adjacent sloped surface $184D_{S3}$ of the side member 180D of the third element 170. As the second element 140 moves distally, the interaction of these sloped surfaces $154_{S1}$, $184D_{S3}$ results in the vertical displacement of the third element 170. The third element 170 may also interface with sloped surfaces of the first element 110 to further encourage this vertical displacement. For example, the first element 110 includes a sloped surface 110S adjacent to a sloped surface $184D_{S1}$ associated with side member 180D, the interaction of the sloped surfaces $110_S$, $184D_{S1}$ further encouraging vertical displacement of the third element 170 as the second element 140 translates distally within the first element 110.

With reference now to FIGS. 5A and 5B, the interaction of first element 110 and the third element 170 will be described in greater detail. For discussion purposes only, the second element 140 has been removed. Additionally, while this discussion considers only a single side member 180D, this discussion also applies to other side members 180 of the third element 170. As depicted, side member 180D includes protrusions 184D and depressions 186D, the protrusions 184D defining corresponding surfaces $184D_{S1-S3}$. The first element 110 includes protrusions 124B and depressions 126B on the inner surface of side portion 118. Protrusion 124B1 includes a surface $124B1_S$, and protrusion 124B2 includes a first surface $124B2_{S1}$ and a second surface $124B2_{S2}$, surface $184D_{S1}$ interfacing with surface $124B1_S$ and surface $184D_{S2}$ interfacing with surface $124B2_{S1}$, such that a portion of side member 180D is able to move within and along depression 126B1. Side member 180D also defines a surface $184DS_3$ that, along with surface $184CS_1$ of side member 184C, interfaces with corresponding surfaces of second element 140, as discussed below with reference to FIG. 6.

Figure 6:
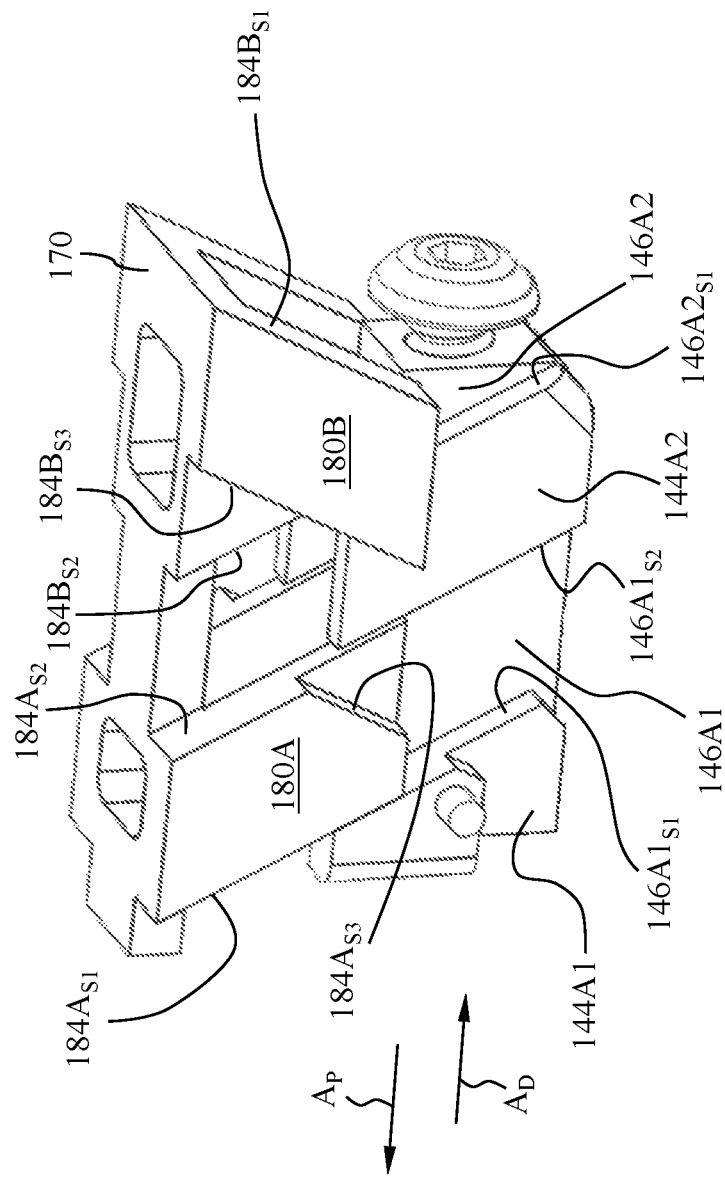
FIG. 6 is a portion of the intervertebral device of FIG. 2.

Turning to FIG. 6, interaction between the geometric features of the second element 140 and the third element 170 are depicted and, for discussion purposes only, the first element 110 has been removed. Additionally, while this discussion considers only a single side portion 150A of the second element 140 and its interaction with side members 180A, 180B of the third element 170, this discussion also applies to side portion 150B of the second element 140 and its corresponding interaction with side members 180C, 180D of the third element 170. As depicted, side portion 150A includes first and second protrusions 144A1, 144A2, and first and second depressions 146A1, 146A2. The side member 180A of the third element 170 includes protrusion 184A having a first side surface $184A_S$, and a second side surface $184A_{S2}$. The first depression 146A1 of the second element 140 includes a first side surface $146A1_{S1i}$ and a second side surface $146A1_{S2}$. The side member 180A of the third element 170 is slidably received in the depression 146A1 of the second element 140, the surfaces $184A_{S1}$, $184A_{S2}$ interfacing with surfaces $146A1_{S1}$, $146A1_{S2}$, respectively. Accordingly, as the second element 140 distally translates in a direction generally depicted by arrow $A_D$, side surface $146A1_{S1}$ couples with side surface $184A_{S1}$ to move the third element 170 at least vertically away from the second element 140. Similarly, as the second element 140 proximally translates in a direction generally depicted by arrow $A_P$, side surface $146A1_{S2}$ couples with side surface $184A_{S2}$ to move the third element 170 at least vertically toward the second element 140.

Figure 7:
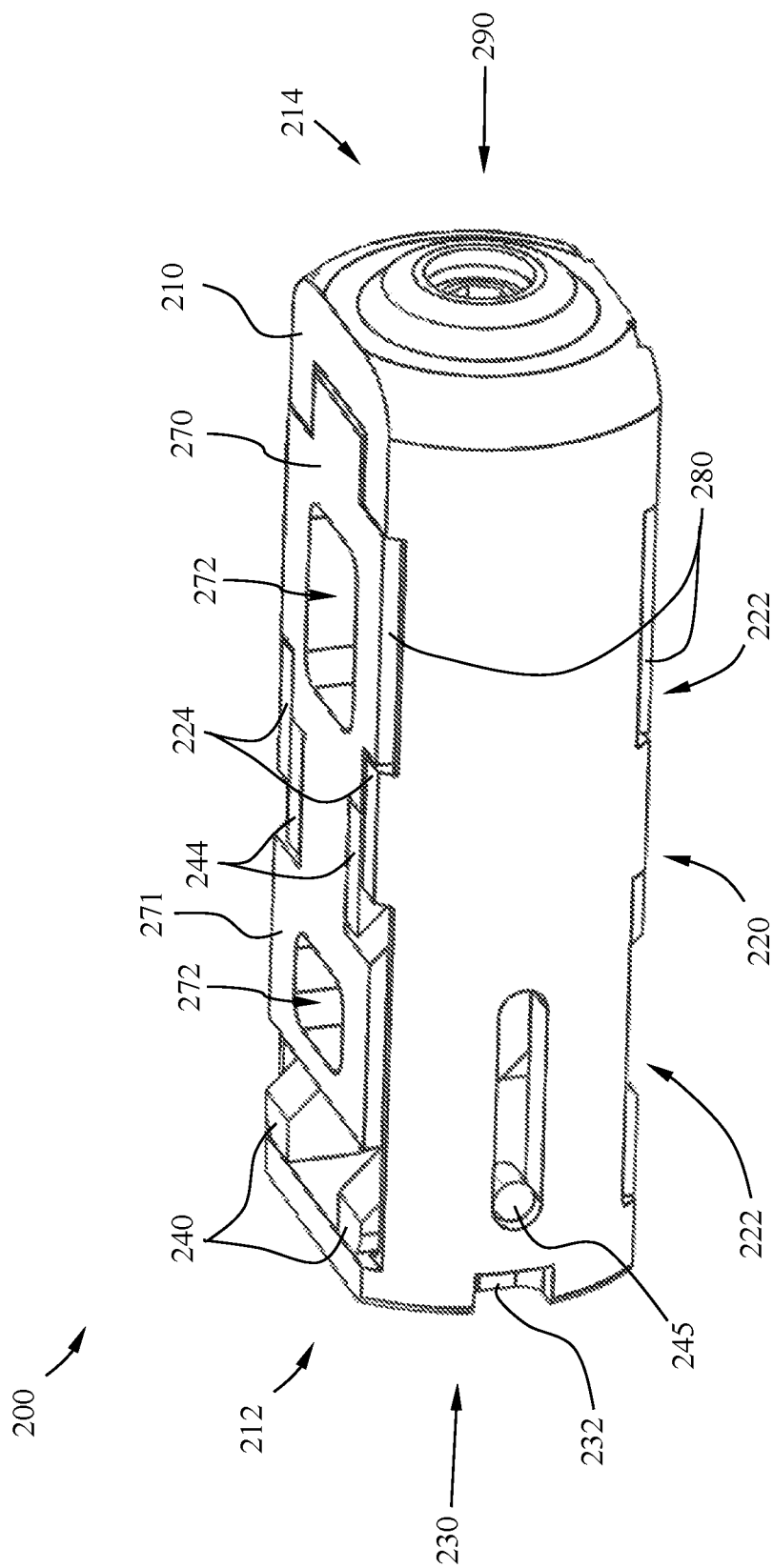
FIG. 7 is a perspective view of another intervertebral device.

Turning to FIG. 7, an exemplary intervertebral device 200 includes a first element 210, a second element 240, a third element 270, and a drive mechanism 290. Intervertebral device 200 is similar to intervertebral device 100, except the elements 210, 240, 270 of the device 200 have geometric characteristics that cooperate in such a way as to allow, in operation, the third element 270 to move vertically with respect to a longitudinal axis of the first element 210. The various surfaces of the element 110, 140, 170 of the device 100 cooperated to allow, in operation, the third element 170 to move vertically, as well as horizontally, with respect to a longitudinal axis of the first element 110.

Element 210 includes a proximal end 212 and a distal end 214, and a first side 216 and a second side 218. The element 210 further includes a bottom portion 220 having one or more openings 222. The element 210 also includes an opening 230 at the proximal end 212, the opening allowing a passageway for medical tools or therapeutic agents to an interior void 202 of the device 200. The second element 240 is similar to element 140, having geometric structures and surfaces that interface with the third element, to allow for the third element to move vertically with respect to a longitudinal axis of the first element 210. The third element 270 has a surface 271 adapted to engage a biological tissue surface, the element 270 including one or more openings 272 in fluid communication with the interior void 202 and the one or more openings 222 of the bottom surface 220 of the first element 210. Third element 270 further includes an side member 280B that has vertical surfaces to encourage vertical movement of the third element 270 with respect to the first element when operated.

Figure 8:
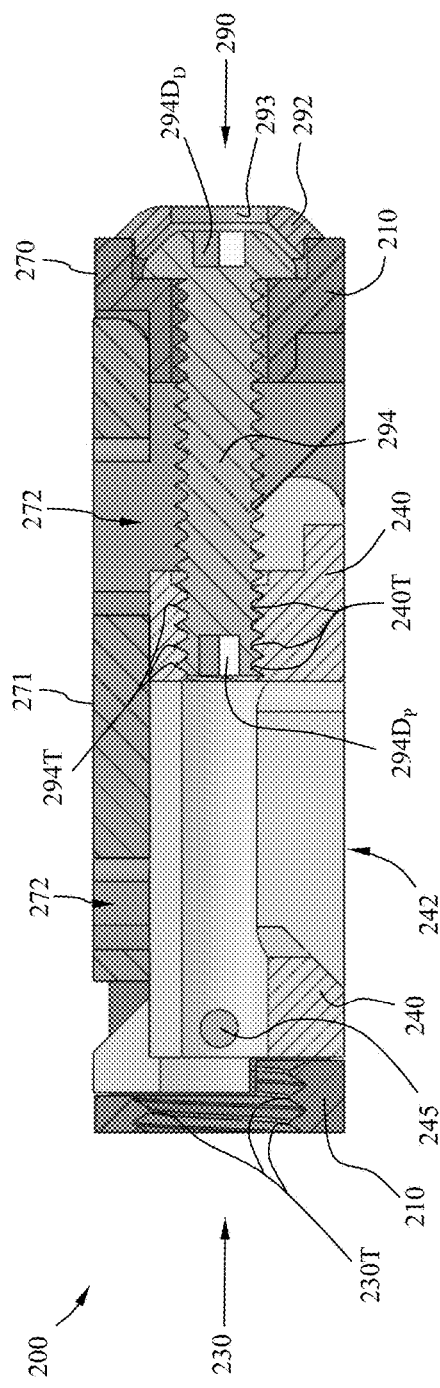
FIG. 8 is a partial section view of the intervertebral device of FIG. 1.
Figure 9:
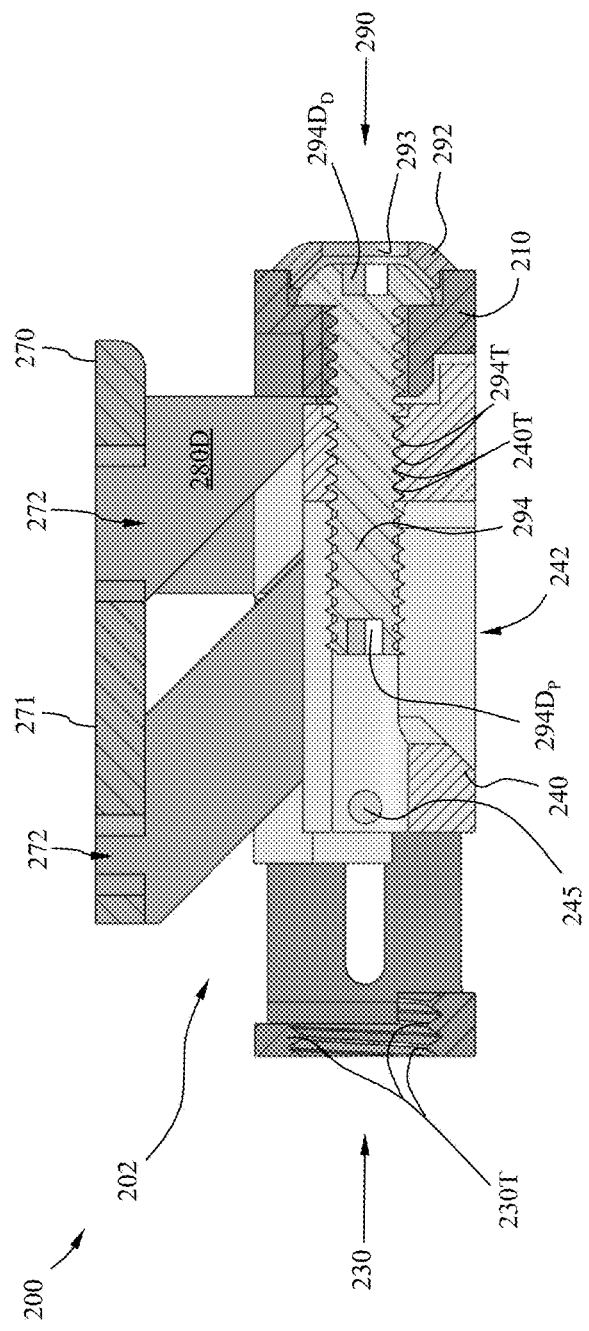
FIG. 9 is another partial section view of the intervertebral device of FIG. 1, in a different configuration.

Turning to FIGS. 8 and 9, the intervertebral device 200 is depicted in cross-section along a central longitudinal axis. As shown, the device 200 includes drive mechanism 290 that includes a retaining cap 292 and drive member 294, similar to the drive mechanism 190 of the intervertebral device 100. The drive member 294 may include drive points 294D configured to receive a driver for rotational control of the member 294. The retaining cap 292 may be fixedly attached to the first element 200 to retain the drive member 294 within the intervertebral device 200 and provide a surface force to allow for the translation of the second element 240. For example, as depicted, the drive member 294 may include a proximal drive point $294D_P$ located closer to proximal end 212 of the first element 210, and a distal drive point $294D_D$ located closer to distal end 212 of the first element 210. Similar to operation of the drive mechanism 190, a driver may enter through opening 230, pass partially through void 202, and engage the proximal drive point $294D_P$, rotation of the driver resulting in corresponding rotation of the driver member 294, for example. The retaining cap 292 may include an opening 293 for driver access to the distal drive point $294D_D$, if desired.

The driver member 294 includes a helical threaded portion 294T configured or adapted to interface with a helical threaded portion 240T of the second element 240. Accordingly, rotation of the drive member 294 results in axial movement of the second member 240. More specifically, if the drive member 294 is rotated in a first direction, the second element 240 will move in a distal direction, toward distal end 214 of the first element 210, and if the drive member 294 is rotated in a second opposing direction, the second element 240 will move in a proximal direction, toward proximal end 212 of the first element 210. Since the threads 294T, 240T are continuous, the second element 240 may be positioned at any point along a longitudinal axis of the first element 210, each point along the longitudinal axis corresponding to a respective height of the third element 270.

Figure 10:
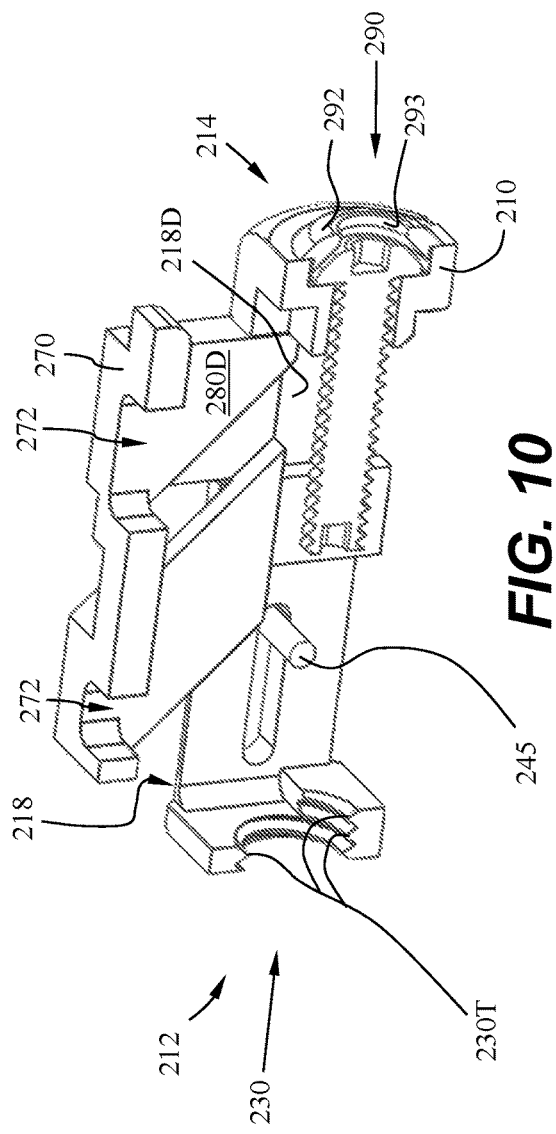
FIG. 10 is a partial section view of a portion of the intervertebral device of FIG. 9.
Figure 11:
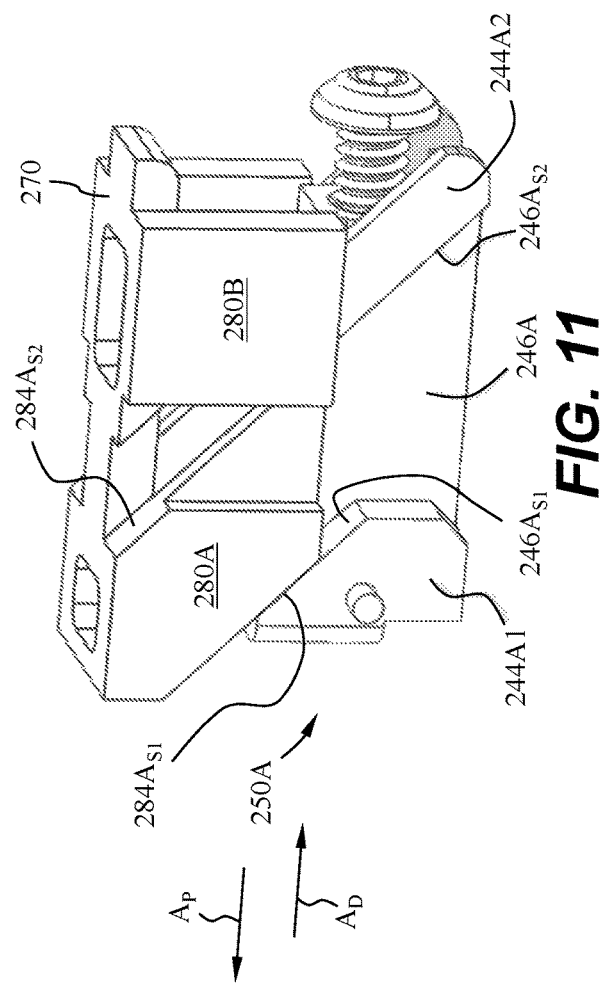
FIG. 11 is another partial section view of a portion of the intervertebral device of FIG. 9.

As shown in FIG. 9, the third element 270 includes a side member 280D that includes side surfaces which are vertical with respect to a longitudinal axis of the first element 210. The side member 280D, during operation, moves vertically in a corresponding depression 218D in the inner wall service of side 218. Turning to FIG. 10, the interaction of the first element 210 and the third element 270 of the intervertebral device 200 is depicted in greater detail, the second element 240 removed for discussion purposes only. As shown, the side member 280D is slidably positioned within the depression 218D. Turning also to FIG. 11, the interaction between the geometric features of the second element 240 and the third element 270 are depicted and, for discussion purposes only, the first element 210 has been removed. Additionally, while this discussion considers only a single side portion 250A of the second element 240 and its interaction with side members 280A, 280B of the third element 270, this discussion also applies to side portion 250B of the second element 240 and its corresponding interaction with side members 280C, 280D of the third element 270. As depicted, side portion 250A includes first and second protrusions 244A1, 244A2, and a depression 246A. The side member 280A of the third element 270 includes protrusion 284A having a first side surface $284A_{S1}$ and a second side surface $284A_{S2}$. The depression 246A of the second element 240 includes a first side surface $246A_{S1}$ and a second side surface $246A_{S2}$. The side member 280A of the third element 270 is slidably received in the depression 246A of the second element 240, the surfaces $284A_{S1}$, $284A_{S2}$ interfacing with surfaces $146A_{S1}$, $146A_{S2}$, respectively. Accordingly, as the second element 240 distally translates, as generally depicted by arrow $A_D$, side surface $246A_{S1}$ couples with side surface $284A_{S1}$ to move the third element 270 vertically away from the second element 240. Similarly, as the second element 240 proximally translates in a direction generally depicted by arrow $A_P$, side surface $246A_{S2}$ couples with side surface $284A_{S2}$ to move the third element 270 vertically toward the second element 140.

Figure 12:
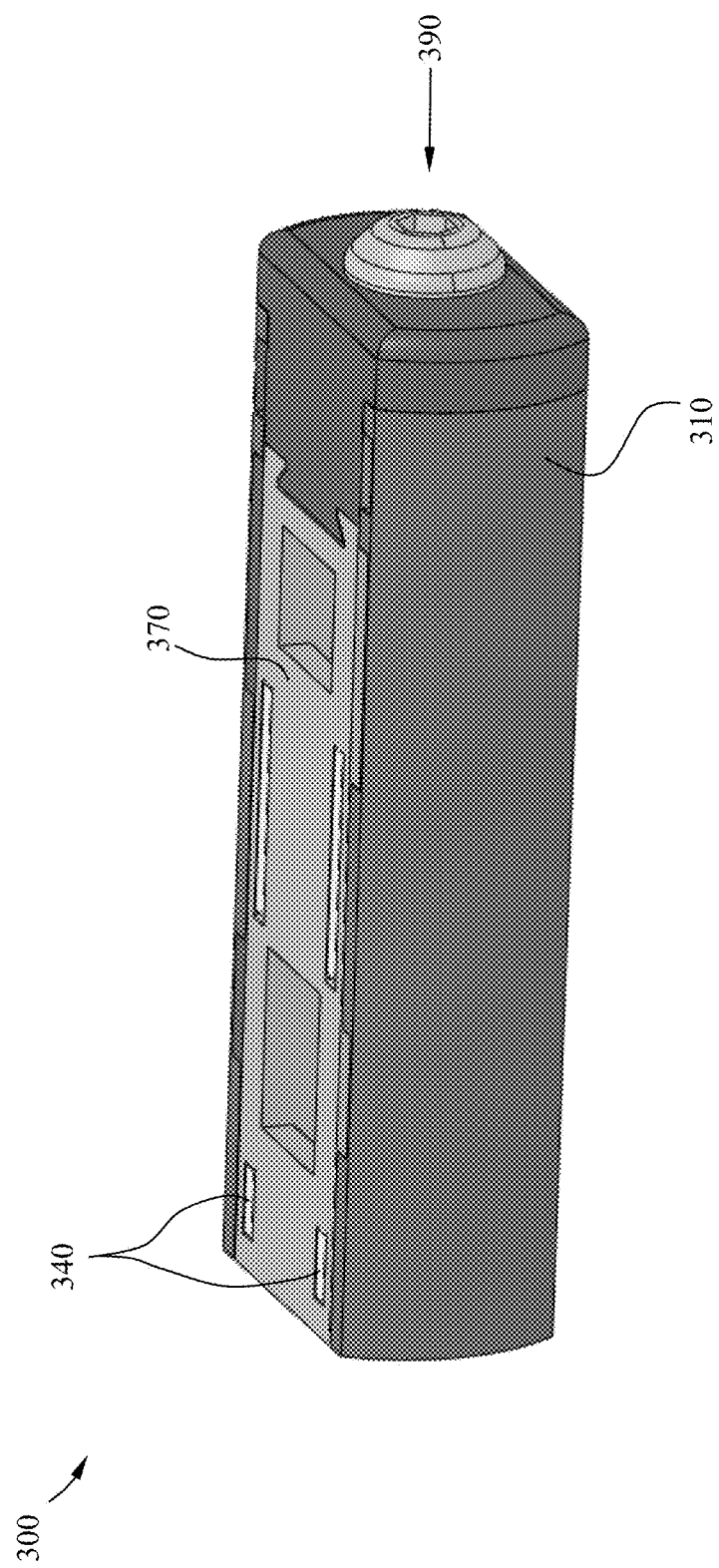
FIG. 12 is a perspective view of an intervertebral device in a first configuration.

Turning to FIG. 12, a third exemplary intervertebral device 300 includes a first element 310, a second element 340, a third element 370, and a drive mechanism 390. Intervertebral device 300 is similar to devices 100 and 200, except as the second element 340 translates distally, both the first element 310 and the third element 370 move vertically away from the second element 340. Turning to FIGS. 13A and 13B, the intervertebral device 300 is depicted in an expanded configuration. As shown, protrusions 344 of the second element 340 are configured to be slidably coupled to corresponding depressions 326 in the first element 310. Additionally, protrusions 384 of side members 380 of the third element 370 are configured to be slidably coupled to corresponding depressions 346 of the second element 340. In a similar fashion as described with respect to the first and second devices 100, 200, as the second element translates distally through operation of the drive mechanism 390, creating or enlarging a void 302, the geometric structures and surfaces of the elements 310, 340, 370 cooperate to move both the first element 310 and the third element 370 vertically away from the second element 340. The configuration of the intervertebral device 300 allows for a greater overall height of device 300 to be achieved with respect to an initial height. Accordingly, the intervertebral device 300 may be initially sized to be delivered through minimally invasive means, e.g. positioned through an endoscopic approach. Once positioned the intervertebral device 300 may then be expanded to a desired height. Turning to FIG. 13C, with the device 300 in an expanded configuration and due to the specific design of the geometric structures of the elements 310, 340, 370, a large void 302 can be achieved. This void 302 can then be filled with therapeutic agents, to encourage healing and/or bone growth around and to the device 300.

Now turning to FIGS. 14 and 15, additional information regarding the operation of intervertebral device 300 will be described. FIG. 14 depicts the device 300 in cross-section, and in a collapsed configuration, while FIG. 15 depicts the device 300 in cross-section, and in an expanded configuration. As shown, intervertebral device 300 includes an alternative element 310A within which a distal portion of the second element translates. Element 310A is vertically slidable with respect to the first element 310 and the third element 350. As with the drive mechanism 190, drive member 394 includes a helical thread 394T that interfaces with corresponding helical thread 340T of the second element 340. Rotation of the drive member in a first direction results in distal movement of the second element 340 with respect to the element 310A. Rotation of the drive member in a second opposing direction results in a proximal movement of the second element 340 with respect to the element 310A. The second element 340 includes multiples protrusions 344B1-344B3, as well as multiple depressions 346B1-346B3, which interface or couple with corresponding depressions and protrusions of the third element 370 in a similar fashion as describes above with respect to intervertebral devices 100 and 200. The second element 340 includes additional multiple protrusions 344D and depressions 346D on the opposing surface of side member 340B, which interface or couple with corresponding protrusions 324B1-B3 and depressions 326B1-B2, respectively. As with other intervertebral devices described or discussed herein, the protrusions and depressions of the elements 310, 340, 370 cooperate such that as the second element 340 translates distally, various surfaces of the protrusions and depressions interface or couple such that the first element 310 moves at least vertically away from the second element 340, and the third element 370 moves at least vertically away in an opposing direction. With the intervertebral device 300 in an expanded configuration the void 302 is maximized allowing for therapeutic agents to be deployed therein, the therapeutic agents exiting various openings, such as openings 372, 322, to encourage bone growth around or adjacent to the device 300. As the second element 340 translates in a proximal direction, the protrusions and depressions of the elements 310, 340, 370 cooperate to take on a more collapsed configuration.

Figure 16:
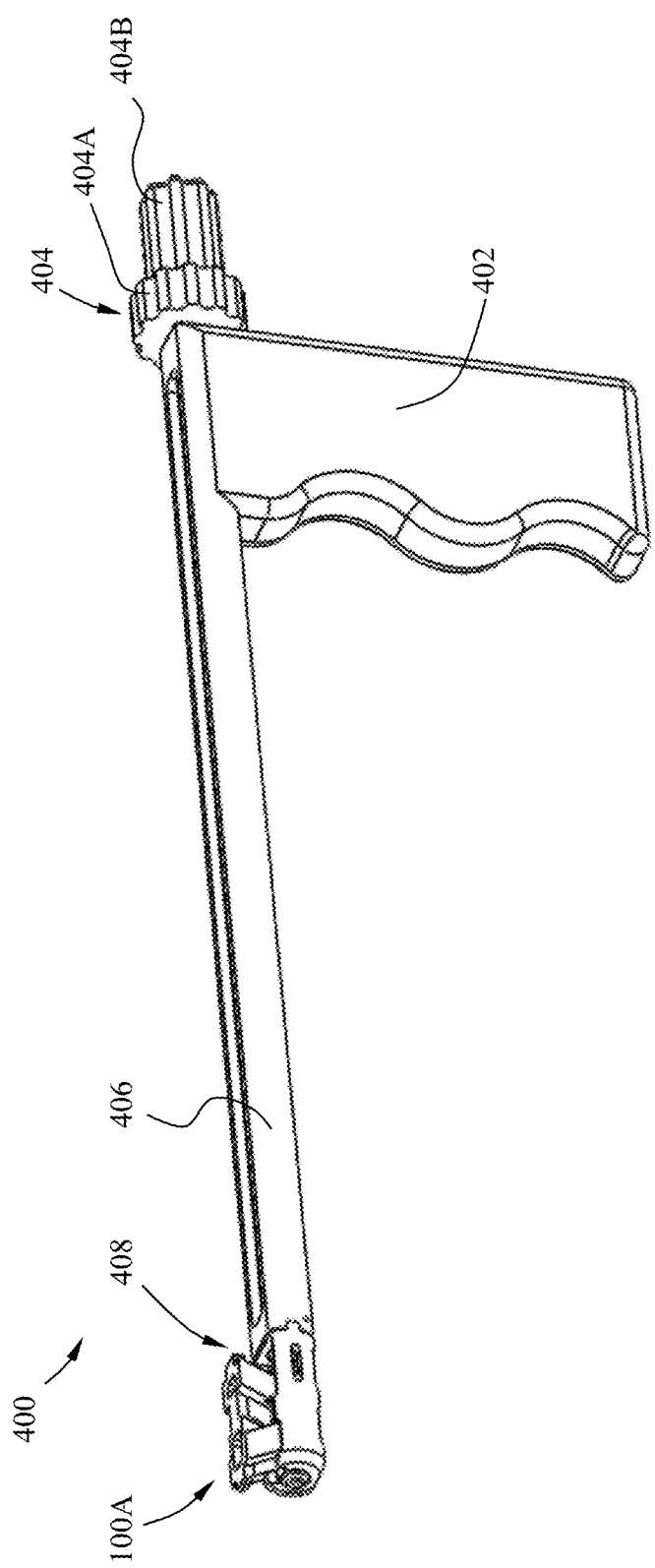
FIG. 16 is a perspective view of an exemplary delivery device.

Turning now to FIG. 16, a delivery system 400 may be used to position intervertebral devices 100, 200, 300, or any other intervertebral devices discussed or contemplated herein, between two adjacent vertebrae, and adjust the height of the corresponding device 100, 200, 300 as desired. While the delivery system 400 is depicted and discussed with respect to an intervertebral device 100A depicted in FIGS. 18-21, such discussion and corresponding operation applies to any intervertebral devices any other intervertebral devices discussed or contemplated herein. The delivery system 400 includes a handle 402, operational controls 404 and an elongated portion 406 ending in a distal portion 408. The distal portion 408 of the delivery system 400 is configured to engage and position an intervertebral device, such as device 100A, within a patient's body. A first operational control 404A is coupled to a first elongate member 410A (not shown) extending within the elongate portion 406, from the control 404A to the distal end 408, a distal end of the elongate member 410A configured to couple the delivery system 400 to the intervertebral device 100A. A second operation control 404B is coupled to a second elongate member 410B (not shown) extending within the elongate portion 406, from the control 404B to the distal end 408, the distal end of the elongate member 410B configured to operate the intervertebral device 100A, e.g. adjust a height of the device 100A.

Figure 17:
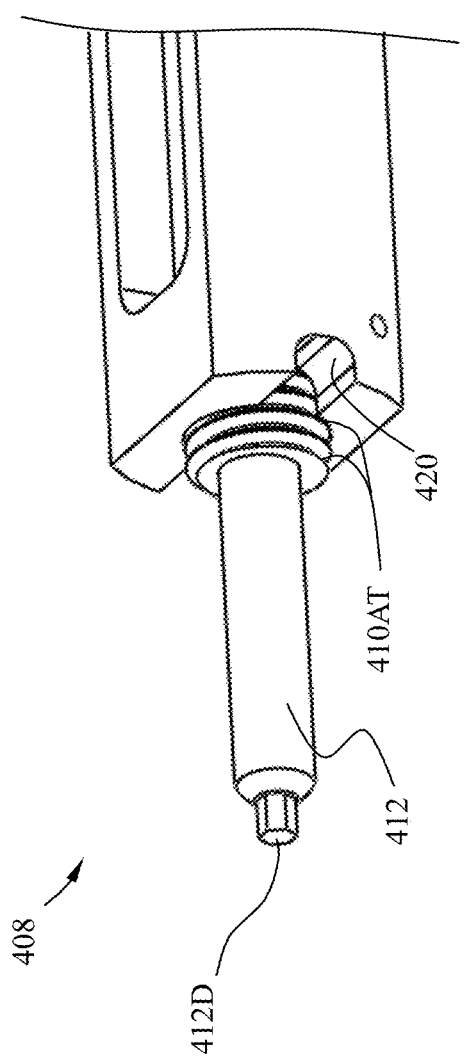
FIG. 17 is a perspective view of a portion of the exemplary delivery device of FIG. 16.
Figure 18:
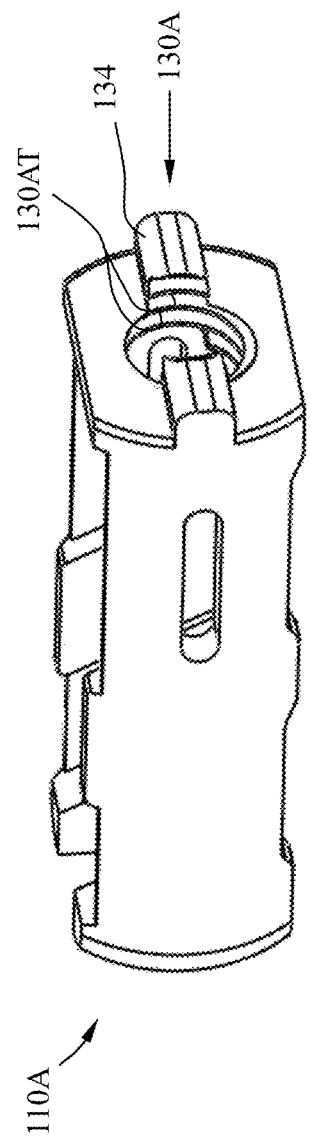
FIG. 18 is a perspective view of an element of an exemplary intervertebral device.

Turning to FIG. 17, the elongate member 410A ends in a threaded portion 410AT at the distal portion 408, and elongate member 410B ends in distal portion 412 including a distal driver 412D. The elongate member 410A is rotatably slidable to elongate member 410B. The distal portion 408 may also include one or more mating structures 420 for engaging similar mating structures as part of the intervertebral device 110A, one or more mating structures 134 as shown in FIG. 18 for example. The mating structures 420, 134 enable the delivery system 400 to maintain a desired orientation with respect to the device 110A. The distal end 408 may also include further engaging structures, such as threaded portion 410AT of the elongate member 410A, to maintain a hold on the device 110A during positioning thereof. The distal driver 412D of the distal portion 412 may be configured to enter a void within the intervertebral device 100A and couple with a drive member, e.g. drive member 194 of drive mechanism 190A.

Figure 19:
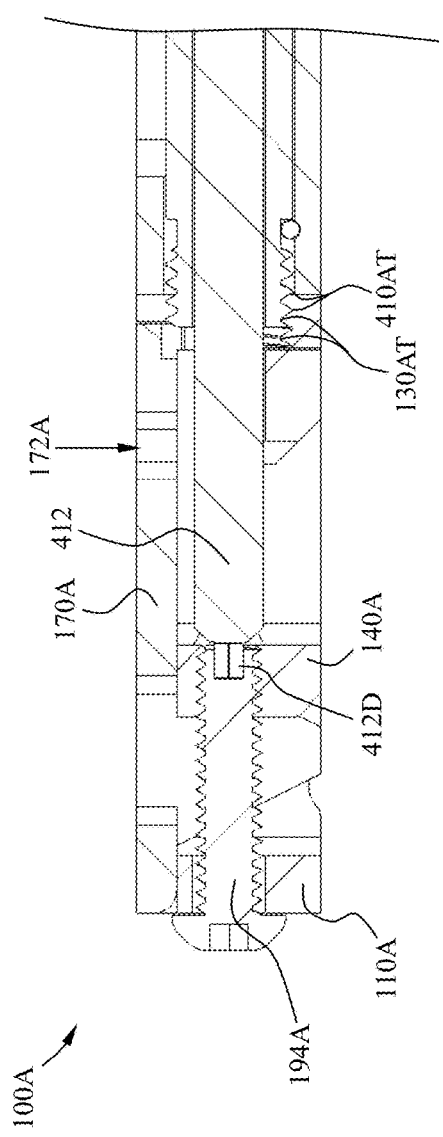
FIG. 19 is a partial section view of an interface between the portion of the exemplary delivery device of FIG. 17 and an exemplary intervertebral device.
Figure 20:
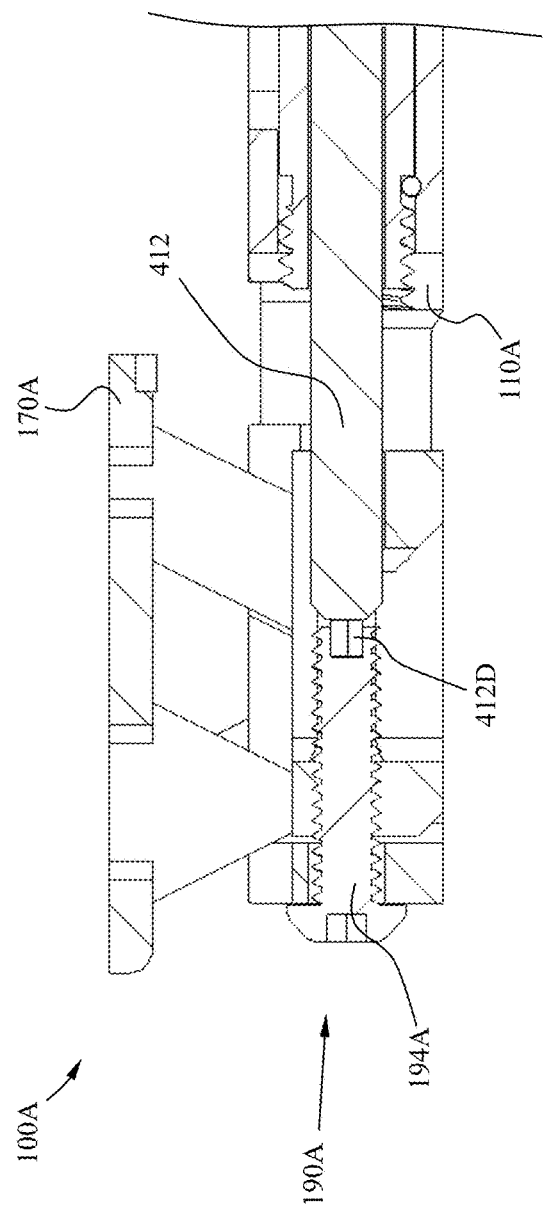
FIG. 20 is another partial section view of an interface between the portion of the exemplary delivery device of FIG. 17 and an exemplary intervertebral device.

Turning to FIG. 19, operation of the first control 404A may act to rotate the threaded portion 410AT of the elongate member 410A, the threaded portion 410AT interfacing to the threaded portion 130T of the first element 110A of the intervertebral device 100A to fixedly attach the device 100A to the delivery system 400. Once the device 100A is positioned within a body, between adjacent vertebrae for example, the second control 404B may be operated to rotate the driver 412D of the device 400, rotation of the driver 412D acting to rotate drive member 194A resulting in adjustment of the overall height, H, of the intervertebral device 100A, as described above with respect to intervertebral device 100. Turning also to FIG. 20, FIG. 20 depicts the intervertebral device 100A in an expanded configuration, the second element 140 moving to a distal end of the first element 110A.

Figure 21:
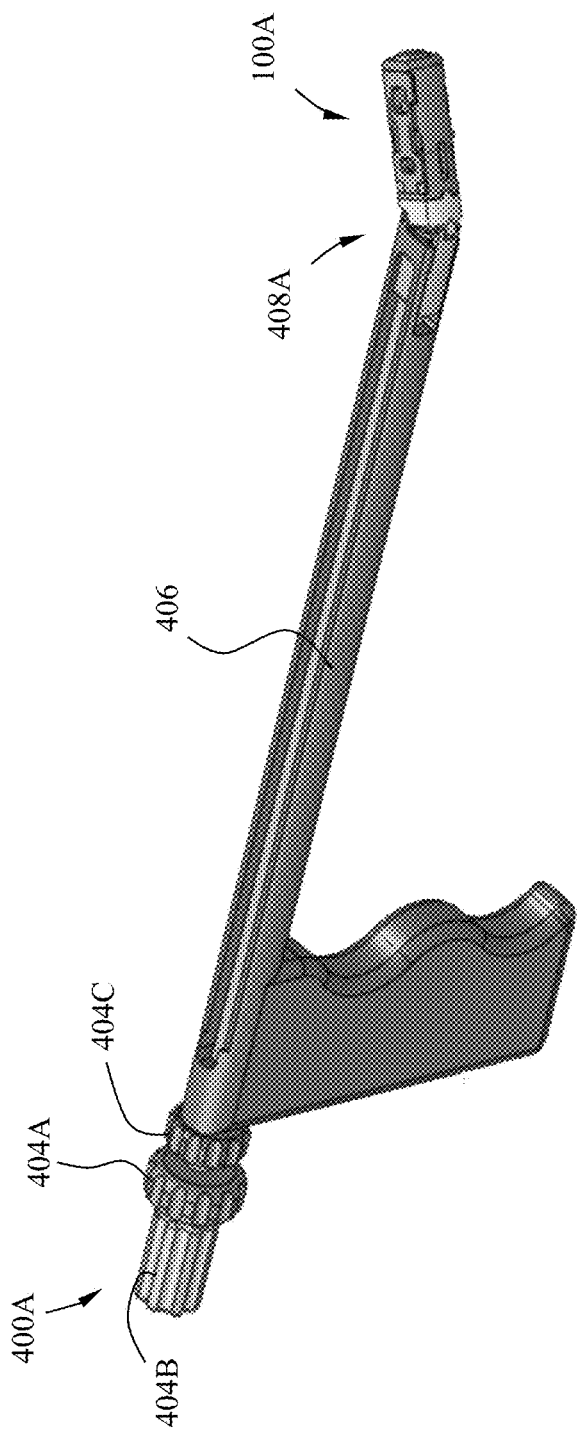
FIG. 21 is a perspective view of another exemplary delivery device.

Turning now to FIG. 21, an alternative delivery system 400A is similar to the delivery system 400 of FIG. 16, however includes a third control 404C that operates a deflectable distal portion 408A. Turning to FIG. 22, control 404C is coupled to the elongate member 406A through threaded portion 404CT that interfaces with threaded portion 406AT. Control 404C is further coupled to a proximal end of an elongate member 410C. Elongate member 406 is coupled to distal portion 408A through a hinge 416. A distal end of the elongate member 410C is coupled to distal portion 408A of delivery system 400A through a hinge 418. Distal portion 408A is also coupled to a central lumen of an elongate member 410A through gear 414. Accordingly, rotation of the control 404C is converted into axial movement of elongate member 410C, which deflects the distal portion 408A with respect to elongate member 406A, as depicted in FIG. 23. Elongate member 410A may include a stop 420 to prevent or limit axial movement of the elongate member 410C, which ultimately limits the deflection of the distal end 408A.

Figure 24:
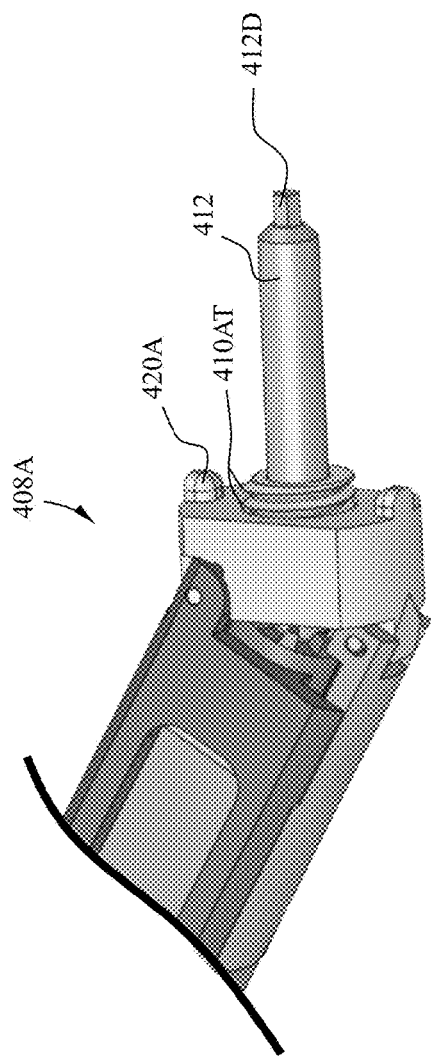
FIG. 24 is a perspective view of a portion of the exemplary delivery device of FIG. 21.
Figure 25:
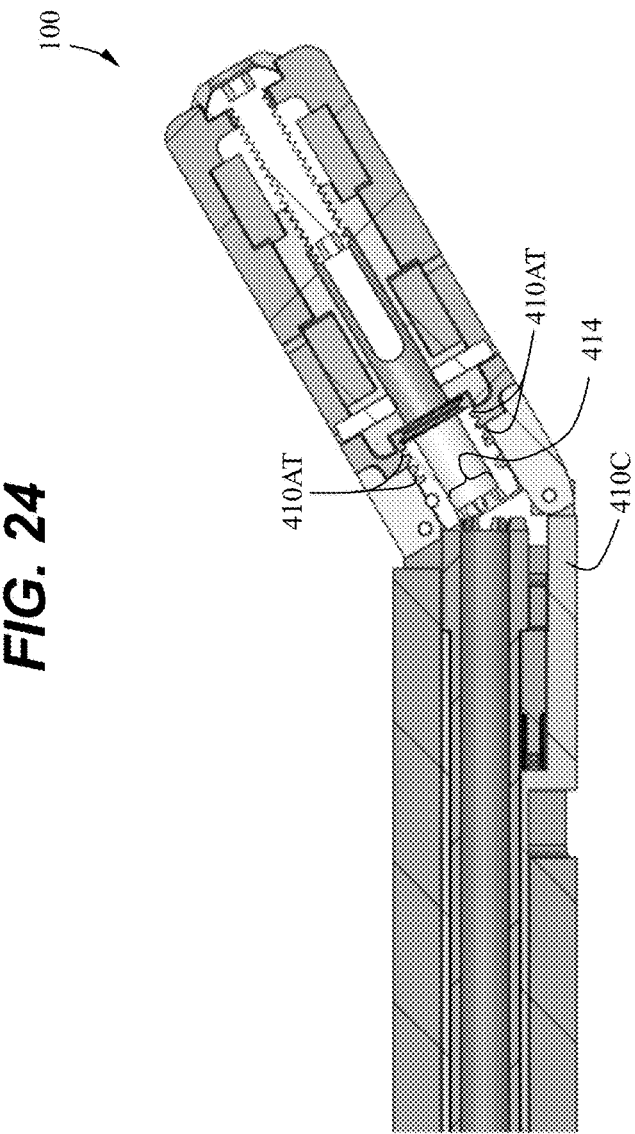
FIG. 25 is another partial section view of a portion of the exemplary delivery device of FIG. 21.

FIG. 24 depicts the distal portion 408A deflected and placement of elongate member 410B, which ends in distal portion 412 and driver 412D. As shown, the distal portion 408A includes one or more protrusions 420A which are configured to engage corresponding recesses on the intervertebral device, such as device 100 for example. The elongate member 410B may include a flexible portion positioned adjacent to the gear 414 such that the member 410B bends with the deflection of the distal portion 408A. FIG. 25 depicts the delivery system 400A interfaced to an exemplary intervertebral device, such as intervertebral device 100. The elongate member 410B has been removed for illustration purposes only. In operation, the driver 412D of the distal end 412 of the elongate member 410B would interface with a drive member of the intervertebral device, the delivery system 400A adjusting a height of the intervertebral device, as described above.

Figure 26:
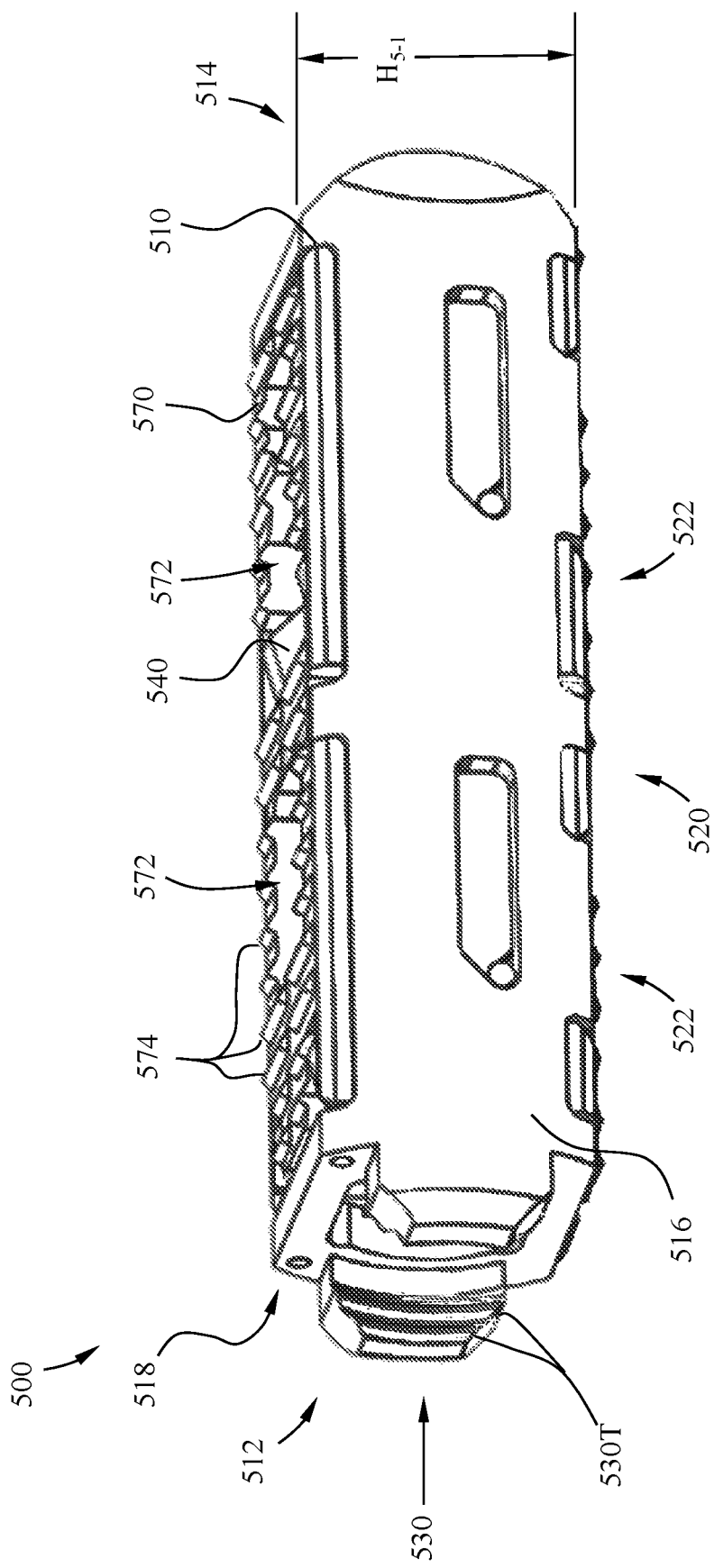
FIG. 26 is a perspective view of another intervertebral device in a first configuration.
Figure 27B:
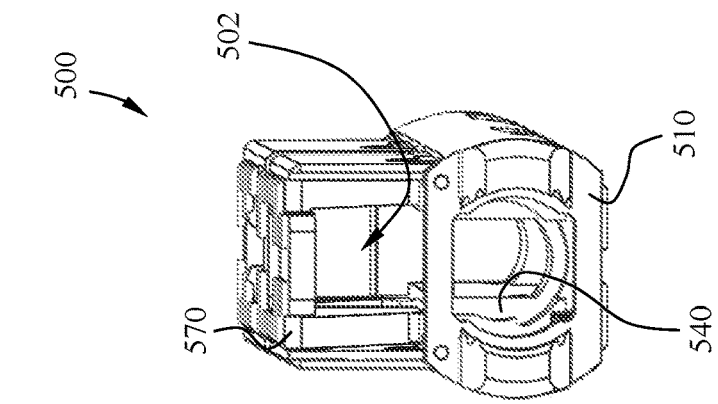
FIGS. 27A and 27B are perspective views of the intervertebral device of FIG. 26 in a second configuration.
Figure 27A:
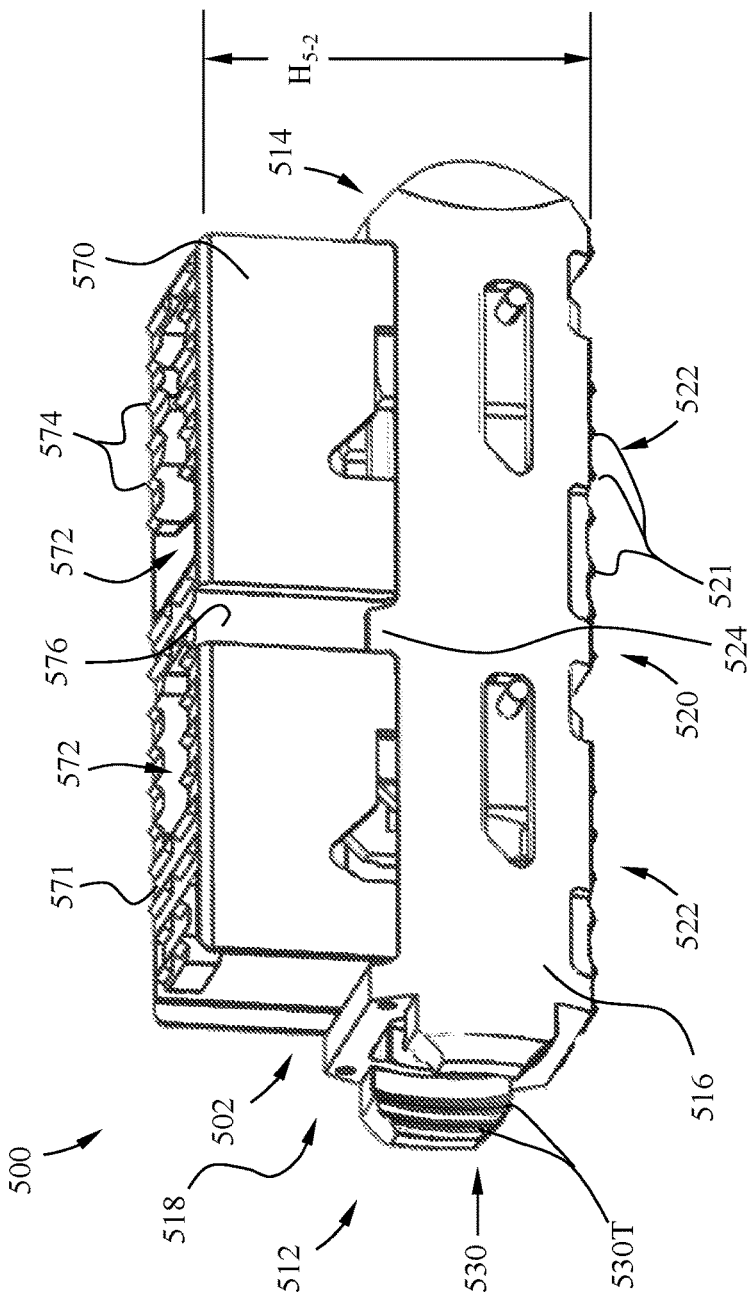

Turning to FIGS. 26 and 27A, a perspective view of an exemplary intervertebral device 500 includes a first element 510, a second element 540, and a third element 570. As will be better understood in the discussion below, the elements 510, 540, 570 cooperate such that the intervertebral device 500 geometric height may have a minimum, collapsed configuration, as generally depicted in FIG. 26, and a maximum, expanded configuration, as generally depicted in FIG. 27A and discussed in greater detail below.

The first element 510, which may also referred to as base 510 or base element 510, is configured to provide a base or outer structure for the intervertebral device 500, and includes a first end 512, a second end 514, and two side portions, a first side portion 516 and an opposing side portion 518. A bottom portion 520 includes one or more openings 522 allowing for therapeutic agents or materials, including bone growth enhancing materials, to pass therethrough. It should be readily understood that the second and third elements 540, 570 may also include similar openings. A proximal end, e.g. end 512, may include an opening 530 for passing a portion of one or more tools utilized for delivery of said therapeutic agents, or expanding, contracting, or locking the intervertebral device 500 in a specific configuration, as is discussed in greater detail below with reference to FIGS. 30A-30C.

The intervertebral device 500 may be expanded or contracted to any suitable height, H, between a first collapsed height $H_{5-1}$ and a second expanded height $H_{5-2}$, with reference to FIGS. 26 and 27A, respectively. For example, the intervertebral device 500 may be expanded from a first position, having the height of $H_{5-1}$ in FIG. 26, to a second position, having the height of $H_{5-2}$ in FIG. 27A, or any height therebetween, and locked in any position. As stated above, the term "lock", "locked" or "locking used in conjunction with the intervertebral device 500, or other intervertebral devices described or contemplated herein, shall mean to substantially maintain the position of each of the elements 510, 540, 570 with respect to each other. The end 512 may also include structures, such as threaded structure 530T, which may allow for attachment points to a delivery system, as described above with respect to intervertebral device 100, for example. Such attachment points may also form the basis for at least initially positioning the intervertebral device 500, for example positioning the device 500 between two adjacent vertebrae. The elements 510, 540, 570 are configured to create a void 502 within the intervertebral device 500, the void 502 increasing during expansion of the intervertebral device 500 from a collapsed configuration to an expanded configuration, for example. In other delivery system embodiments, the delivery system may include tubular members through which therapeutic agents may be introduced, for example, to internal spaces or voids within the intervertebral device 500 and exiting through the one or more openings 522 of the element 510, or similar openings of the remaining elements 540, 570. In this way, such therapeutic agents may contact surrounding tissues, such as bone tissue of the vertebra.

The third element 570 is slidably interfaced to the first element 510 such that the third element 570 at least slides vertically with respect to the first element 510. The third element 570 may include one or more openings 572 in a top portion or top surface 571 thereof to allow for passage or introduction of therapeutic agents therethrough. The top portion 571 may include one or more protrusions 574 that may aide in holding the top portion 571 immobile with respect to adjacent structures or biological tissue, such as vertebrae structures for example. While only a few protrusions 574 are identified, additional or less protrusions 574 may be utilized. Additionally such protrusions, like protrusions 574, may be constructed from any biocompatible material and in any suitable form, and may be used with other elements or surfaces of intervertebral device 500, or any other intervertebral device described or contemplated herein. For example, sidewalls 516, 518 of element 510 may include one or more protrusions (not shown), similar to protrusions 574, and a bottom portion 520 of base 510 may include one or more protrusions, similar to protrusions 574.

Turning specifically to FIG. 27A, the element 510 may include a positioning structure or protrusion 524 which may be configured or adapted to move within a corresponding channel 576 provided in element 570 to ensure that the element 570 moves in a specific direction with respect to the element 510. Accordingly, channel 576 and associated structure 524 may be configured to form any desirable angle with respect to a longitudinal axis of element 510. As depicted, channel 574 is substantially perpendicular to a longitudinal axis of element 510 and, therefore, the element 570 moves in a direction substantially perpendicular to the longitudinal axis of element 510.

Turning to FIG. 27B, the intervertebral device 500 is depicted in an expanded configuration and the viewpoint is from the first end 512. The elements 510, 540, 570 are configured such that when in an expanded configuration the open space or void 502 is defined, e.g., as seen through opening 530 or opening 572. In this way, once the device 500 is deployed therapeutic agents may be positioned within the void 502 from the first end 512 to the second end 514 and into voids of the other elements 540, 570. Such material may further flow out of the open space via additional openings, such as openings 572 and 522, positioned about the elements 510, 540, 570.

Figure 28:
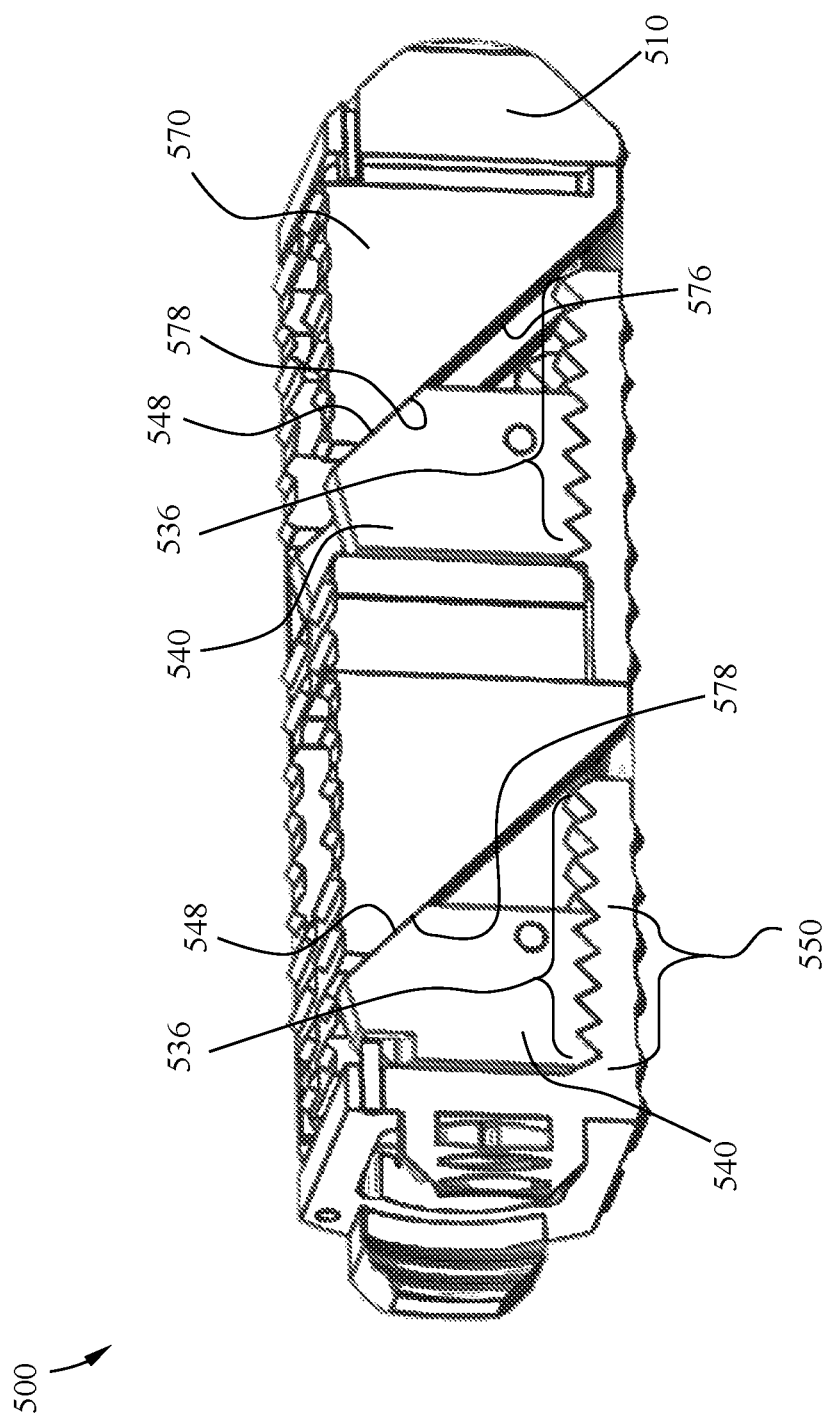
FIG. 28 is a partial section view of the intervertebral device of FIG. 26.

Turning to FIG. 28, an elevation view depicting the elements 510, 540, 570 in cross-section is shown. The third element 570 may include a plurality of sloped surfaces 578 that are configured or adapted to contact a respective one of a plurality of sloped surfaces 548 of second element 540. Accordingly, as the second element or sliding element 540 translates between the first end 512 and the second end 514 of the element 510, the sloped surfaces 548 contact and slide along corresponding respective sloped surfaces 578 of the third element 570 resulting in movement of the element 570 in a direction defined by channel 574, and the sloped surfaces 548, 578. As depicted, translation of sliding element 540 from the first end 512 toward the second end 514 results in movement of the element 570 in a vertical direction away from the base element 510. Translation of the sliding element 540 from the second end 514 toward the first end 512 results in movement of the element 540 in a vertical direction toward the base element 510.

The first element 510 or base element 510 includes a plurality of engaging elements 536 that protrude from a top inner surface of the bottom portion 520 of element 510. Second element 540 includes a plurality of engaging elements 550, at least one engaging a respective one of the plurality of engaging elements 536. While depicted as being integral to the respective elements 510, 540, the engaging elements 536, 550 may be individual parts attached or affixed to the surfaces of the base element 510 and sliding element 540, respectively. The engaging elements 536, 550 are depicted as having similar shapes, e.g., triangular portions, however in other configurations, the shapes can be dissimilar. For example, each of the engaging elements 550 may include a concave surface while each of the engaging elements 536 may include a corresponding mating convex surface. The shapes of the engaging elements 536, 550 may also be non-mating surfaces such that gaps exist at the interface between the engaging elements 536, 550, for example. Also, while depicted as triangular structures, each of the elements 536, 550 may be nonsymmetrical along its vertical central axis, passing through the tip of each element 536, 550.

The intervertebral device 500 is configured such that applying a lateral force to the sliding element 540 to translate the element 540 between the first and second ends 512, 514 of base member 510, results in each engaging element 550 sliding up and over a corresponding engaging element 536, and engaging an adjacent engaging element 536 in the direction of the movement of sliding element 540. Accordingly, sliding element 540, while primarily moving along the longitudinal axis of the base element 510, also move vertically in accordance with the geometry outline and coupling of the engaging elements 550, 536 of the sliding element 540 and base element 510, respectively.

Turning back to FIGS. 26 and 27A, a plurality of pins 544 are coupled to sliding member 540 and extend through corresponding openings 528 in the side portions 516, 518 of base element 510. With the intervertebral device 500 in the collapsed configuration, as depicted in FIG. 26, the sliding element 540 is nearer the first end 512, the pins 544 being nearer the first end 512, as well. With the intervertebral device 500 in the expanded configuration, as depicted in FIG. 27A, the sliding element 540 is nearer the second end 514, the pins 544 being nearer the second end 514 as well. The openings 523 of the first element 510 are spaced to allow some vertical travel of the sliding element 540 and pins 544 in accordance with the geometrical shapes, e.g. height, of the engaging elements 550, 536. It is noted that by adjusting the slope of each side surface of the engaging elements 550, 536 the translational force to move the sliding element 540 in the presence of a compression force between the top portion 571 of element 570 and the bottom portion 520 of the base element 510 may differ in accordance with the corresponding element 550, 536 sloped surfaces. The slopes of each side surface of the engaging elements 550, 536, which may be continuous or may not be continuous, may be configured to encourage movement of the sliding element 540 in a first direction along the longitudinal axis of the base 510 and discourage movement of the sliding element 540 in a second opposite direction. In any case, the engaging elements 550, 536 are configured, e.g., with suitable sloped surfaces or the like, to become locked or immovable when a compression force exists between the third element 570 and the base element 510.

Figure 29:
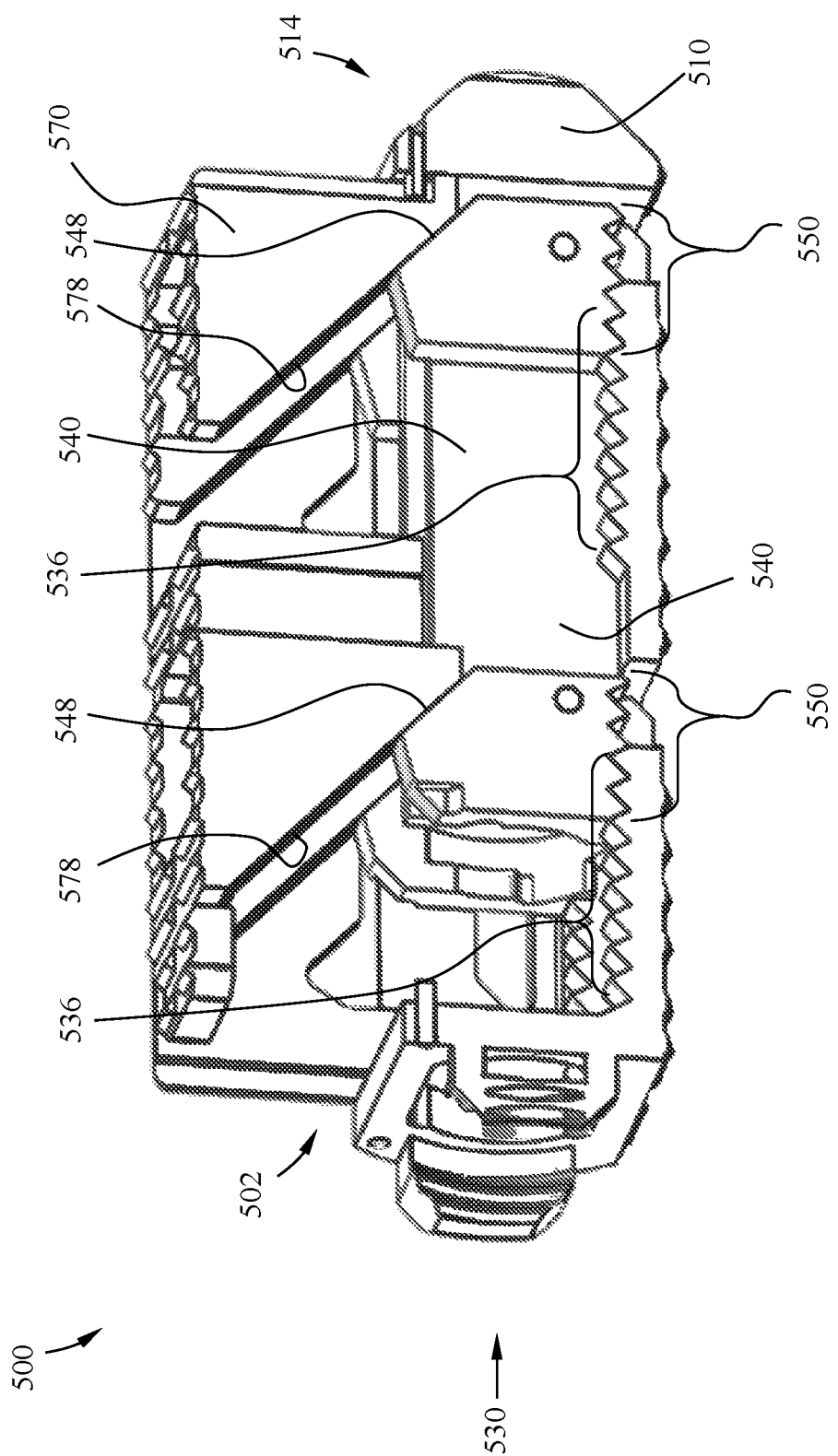
FIG. 29 is a partial section view of the intervertebral device of FIG. 27A.

Turning now to FIG. 29, the intervertebral device 500 is depicted in an expanded configuration. With a lateral force applied to sliding element 540 moving the element 540 toward end 514, in a ratcheting manner, for example, the engaging elements 550, 536 continuously engage and disengage with adjacent opposing engaging elements 550, 536. As the element 540 translates, the third element 570 moves vertically to increase the overall height of the device 500. With a compression force applied between the third element 570 and the base element 510, e.g. when the device 500 is positioned between adjacent tissue surfaces, such as two adjacent vertebrae, the engaging elements 550, 536 of the sliding element 540 and base element 510, respectively, engage and prevent the sliding element 540 to translate further.

Turning to FIGS. 30A-30C, an exemplary tool 600 utilized to translate sliding element 540, or similar sliding elements discussed or described herein, includes a distal end 602 having a protrusion 604 adjacent to a groove 606. The protrusion is adapted to fit a groove 566 at a proximal end of the sliding element 540. As depicted in FIG. 30A, the tool 600 is angled or rotated along its axis such that the protrusion 604 freely enters the proximal end of the sliding element 540, as depicted in FIG. 30B. Once inserted, the tool 600 may be rotated in a direction indicated by arrow 30A such that the protrusion 604 is positioned within the groove 566 of the proximal end of the sliding element 540 and held in place through the cooperation of the protrusion 604 and a protrusion 567 at the proximal end of sliding element 540, as depicted in FIG. 30C.

The groove 566 of the sliding element 540 cooperates with the protrusion 604 of the tool 600 to rigidly attach the tool 600 to the element 540. Once the tool 600 is rigidly attached to the sliding element 540 a user can translate the sliding element 540 through corresponding translation of the tool 600. As described above, translation of the tool 600, which results in the translation of the sliding element 540, further results in the sliding element 540 to move between the ends 512, 514 of the base member 510. As the sliding element 540 translates or moves between the ends 512, 514, the element 570 moves in a vertical direction with respect to the base element 510 to change the overall height, H, of the intervertebral device 500. As should be readily understood, the tool 600 may extend from a point within a body structure to a point outside of the body.

Figure 31:
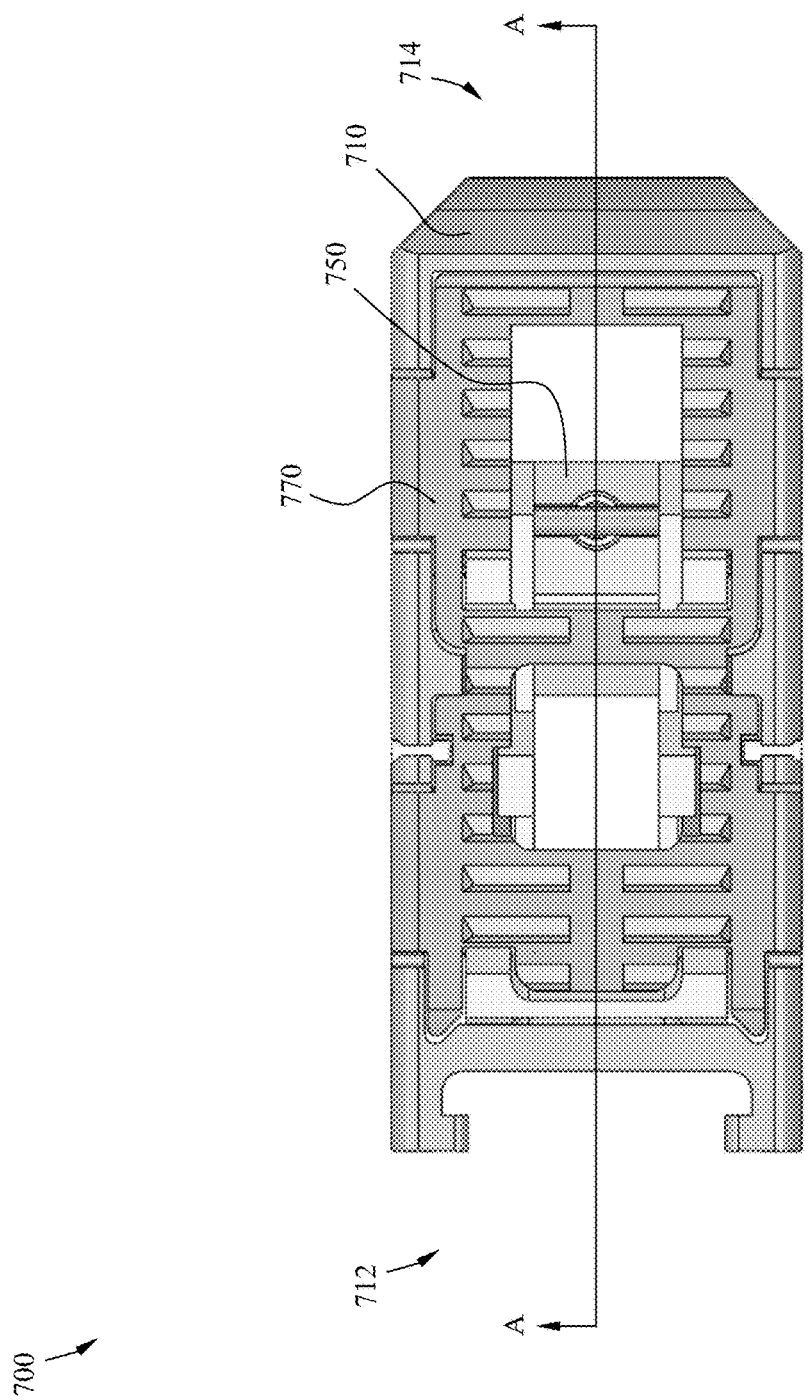
FIG. 31 is a top view of another exemplary intervertebral device.

Turning now to FIG. 31, another exemplary intervertebral device 700 includes a first or base element 710, a second, or sliding element 740, and a third element 770. The intervertebral device 700 is similar to the intervertebral device 500, but the elements 710, 740, 770 of the device 700 include different geometric structures as compared to intervertebral device 500. The intervertebral device 700 includes a distal end 712 and a proximal end 714, the distal end 712 including a different geometric structure used for positioning and operating the device 700.

Figure 32:
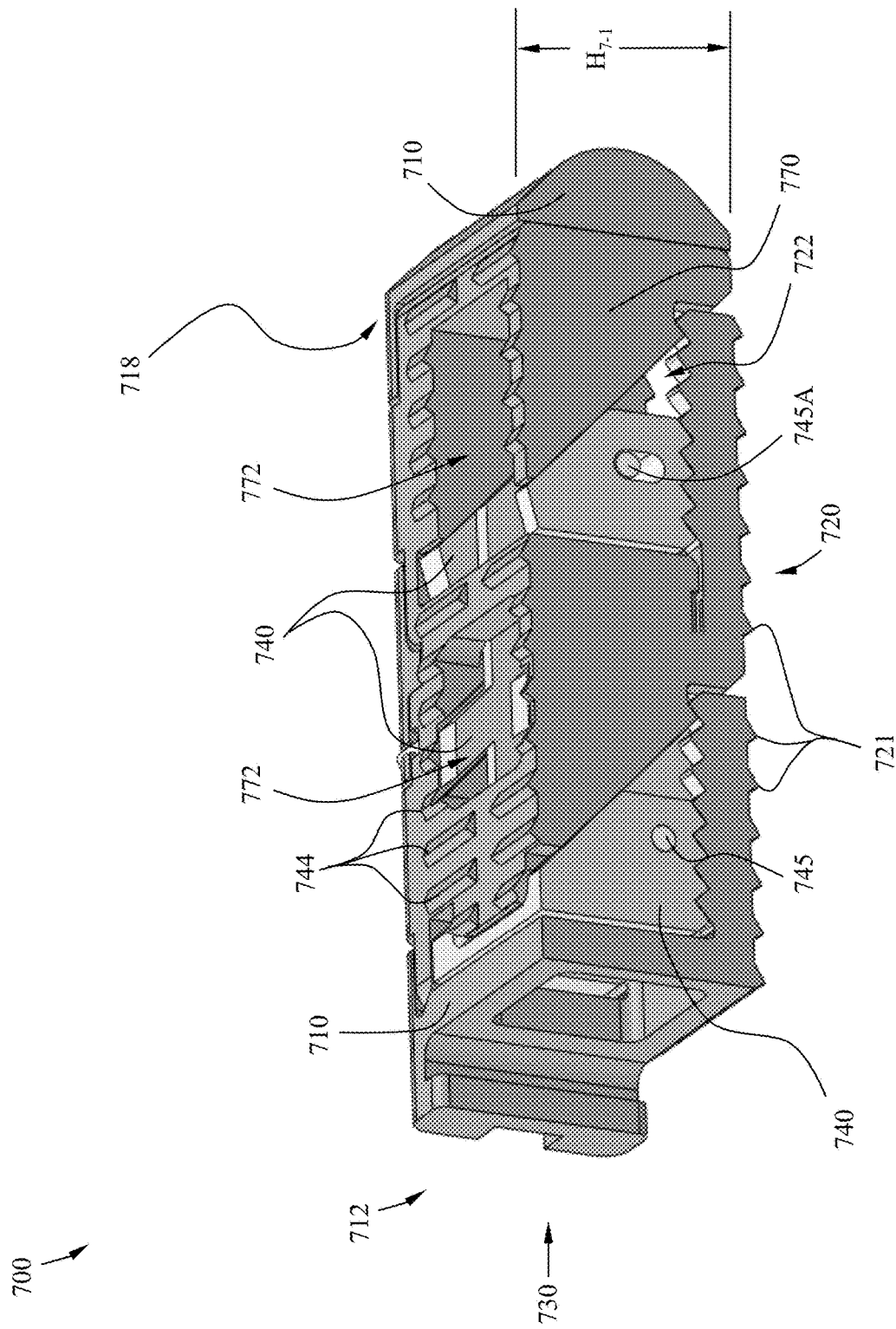
FIG. 32 is a partial section view of the exemplary intervertebral device of FIG. 31.
Figure 33:
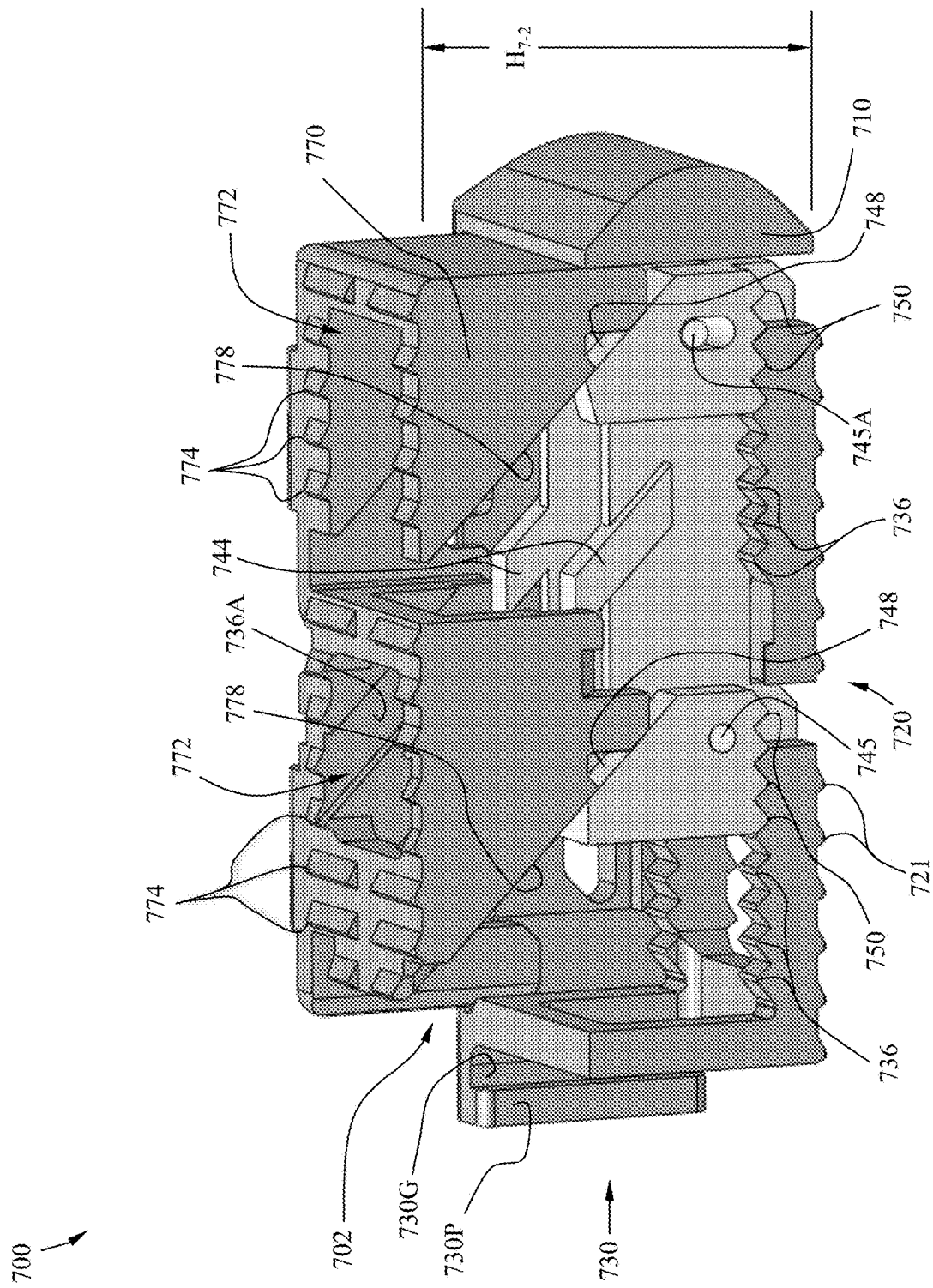
FIG. 33 is another partial section view of the exemplary intervertebral device of FIG. 31.

Turning to FIGS. 32 and 33, a perspective view of the exemplary intervertebral device 700 is depicted in cut view along section A-A of FIG. 31. As with other intervertebral device described or contemplated herein and better understood in light of the discussion below, the elements 710, 740, 770 cooperate such that the intervertebral device 700 geometric height, $H_7$, may have a minimum, collapsed configuration, as generally depicted in FIG. 32, and a maximum, expanded configuration, as generally depicted in FIG. 33 and discussed in greater detail below.

The first element 710, also referred to as base 710 or base element 710, is configured to provide a base or outer structure for the intervertebral device 700, and includes first end 712, second end 714, and two side portions, a first side portion 716 and an opposing side portion 718. A bottom portion 720 includes one or more openings 722 allowing for therapeutic agent to pass therethrough. It should be readily understood that the second and third elements 740, 770 may also include similar openings. The proximal end 712, may include an opening 730 for passing a portion of one or more tools utilized for delivery of said therapeutic materials, or expanding, contracting, or locking the intervertebral device 700 in a specific configuration.

The intervertebral device 700 may be expanded or contracted to any suitable height, $H_7$, between a first collapsed height $H_{7-1}$ and a second expanded height $H_{7-2}$, with reference to FIGS. 32 and 33, respectively. For example, the intervertebral device 700 may be expanded from a first position, having the height of $H_{7-1}$ in FIG. 32, to a second position, having the height of $H_{7-2}$ in FIG. 33, or another position therebetween, and locked in the position. The proximal end 712 may also include structures, such as protrusions 730P and grooves 730G, which may allow for attachment points to a delivery system (not shown), as described below with respect to delivery device 800 of FIG. 38. Such attachment points may also form the basis for at least initially positioning the intervertebral device 700, for example between two adjacent vertebrae. As described in greater detail below, the delivery system 800 may include tubular members through which therapeutic agents may be introduced, for example, to internal spaces within the intervertebral device 700 and exiting through the one or more openings 722 of the element 710, or similar openings of the remaining elements 740, 770. In this way, such agents or materials may contact surrounding tissues, such as bone tissue.

The third element 770 is slidably interfaced to the first element 710 such that the third element 770 at least slides vertically with respect to the first element 710. The third element 770 may include one or more openings 772 in a top portion 771 thereof to allow for passage or introduction of therapeutic elements or bone growth enhancing materials therethrough. The top portion 771 may include one or more protrusions 774 that may aide in holding the top portion 771 immobile with respect to adjacent structures or biological tissue, such as vertebrae structures for example. While only a few protrusions 774 are identified, additional or less protrusions 774 may be utilized. Such protrusion structures 774 may be constructed from any biocompatible material and in any suitable form and may be applied to any embodiment described or contemplated herein. Additionally, sidewalls 716 of element 710 may include one or more protrusions (not shown), and a bottom portion 720 of base 710 may include one or more protrusions 721. Protrusions 721 may, for example, may be similar to protrusions 774, which may aide in holding a bottom portion 720 immobile with respect to adjacent structures or biological tissue, such as vertebrae structures for example.

Turning specifically to FIG. 33, the element 710 may include a positioning structure or protrusion similar to the protrusion 524 of the base element 510 of device 500, which may be configured or adapted to move within a corresponding channel similar to the channel 576 provided in element 570 of device 500, to ensure that the element 770 moves in a specific direction with respect to the element 710. Accordingly, as with the device 500, the channel and associated structure may be configured to form any desirable angle with respect to a longitudinal axis of element 710. The channel of element 770 is substantially perpendicular to a longitudinal axis of element 710 and, therefore, the element 770 moves in a direction substantially perpendicular to the longitudinal axis of element 710.

As with the intervertebral device 500, a void or space 702 is defined by the first, second, and third element 710, 740, 770 of the intervertebral device 700, the void increasing as the device 700 transitions from a collapsed configuration to an expanded configuration. In this way, once the device 700 is deployed therapeutic agents may be positioned within the void 702 from the first end 712 to the second end 714. Such agents may further flow out of the open space via additional openings, such as openings 772 and 722, positioned about the elements 710, 740, 770.

Turning back to both FIGS. 32 and 33, the third element 770 may include a plurality of sloped surfaces 778 that are configured or adapted to contact a respective one of a plurality of sloped surfaces 748 of second element 740. Accordingly, as the second element or sliding element 740 translates between the first end 712 and the second end 714 of the element 710, the sloped surfaces 748 contact and slide along corresponding respective sloped surfaces 778 of the third element 770 resulting in movement of the element 770 in a vertical direction, e.g. defined by a channels and wall structures between the first element 710 and the third element 770. As depicted, translation of sliding element 740 from the first end 712 toward the second end 714 results in movement of the element 770 in a vertical direction away from the base element 710. Translation of the sliding element 570 in a direction from the second end 714 toward the first end 712 results in movement of the element 740 in a vertical direction toward the base element 710.

The first element or base element 710 includes a plurality of engaging elements 736 that protrude from a top inner surface of the bottom portion 720 of element 710. Second element 740 includes a plurality of engaging elements 750, at least one of the elements 750 engaging a respective one of the plurality of engaging elements 736. While depicted as being integral to the respective elements 710, 740, the engaging elements 736, 750 may be individual parts attached or affixed to the surfaces of the base element 710 and sliding element 740, respectively. As with the engaging elements 536, 550 of the intervertebral device 500, the engaging elements 736, 750 are depicted as having similar shapes, e.g., triangular portions, however in other configurations, the shapes can be dissimilar, or may be nonsymmetrical along its vertical central axis, passing through the tip of each element 736, 750.

As with intervertebral device 500, the intervertebral device 700 is configured such that applying a lateral force to the sliding element 740 to translate the element 740 between the first and second ends 712, 714 of base member 710, results in each engaging element 750 sliding up and over a corresponding engaging element 736, and engaging an adjacent engaging element 736 in the direction of the movement of sliding element 740. Accordingly, sliding element 740, while primarily moving along the longitudinal axis of the base element 710, also move vertically in accordance with the geometry outline and coupling of the engaging elements 750, 736 of the sliding element 740 and base element 710, respectively.

The intervertebral device 700 further includes a plurality of pins 745 coupled to sliding member 740 and extending through corresponding openings 728 in the side portions 716, 718 of base element 710. With the intervertebral device 700 in the collapsed configuration, as depicted in FIG. 32, the sliding element 740 is nearer the first end 712, the pins 745 being nearer the first end 712, as well. With the intervertebral device 700 in the expanded configuration, as depicted in FIG. 33, the sliding element 740 is nearer the distal end or second end 714, the pins 745 being nearer the second end 714 as well. The openings 728 of the first element 710 are spaced to allow some vertical travel of the sliding element 740 and pins 745 in accordance with the geometrical shapes, e.g. height, of the engaging elements 750, 736. It is noted that by adjusting the slope of each side surface of the engaging elements 750, 736 the translational force to move the sliding element 740 in the presence of a compression force between the top portion 771 of element 770 and the bottom portion 720 of the base element 710 may differ in accordance with the corresponding element 750, 736 sloped surfaces. The slopes of each side surface of the engaging elements 750, 736, which may be linear or may be nonlinear, may be configured to encourage movement of the sliding element 740 in a first direction along the longitudinal axis of the base 710 with respect to the sliding element 740 in a second opposite direction. In any case, the engaging elements 750, 736 are configured, e.g., with suitable sloped surfaces or the like, to become locked or immovable when a compression force exists between the third element 770 and the base element 710.

Turning specifically to FIG. 33, the sliding element 740 may include a protrusion 744 configured or adapted to slidably interface with a corresponding recessed portion or groove 736A along the inner wall of the third element 770. The protrusion 744 cooperates with recessed portion 736A such that when the sliding element 740 translates in a proximal direction, in a direction toward proximal end 712 of the intervertebral device for example, the surfaces of the protrusion 744 engage surfaces of the recessed portion 736A to encourage the third element 770 to move vertically toward the first element 710.

As with vertebral device 500, in the presence of a lateral force applied to sliding element 740 moving the element 740 toward end 714, in a ratcheting manner, for example, the engaging elements 750, 736 continuously engage and disengage with adjacent opposing engaging elements 750, 736. As the element 740 translates, the third element 770 moves vertically to increase the overall height, $H_7$, of the device 700. With a compression force applied between the third element 770 and the base element 710, e.g. when the device 700 is positioned between adjacent tissue surfaces, such as two adjacent vertebrae, the engaging elements 750, 736 of the sliding element 740 and base element 710, respectively, engage and prevent the sliding element 740 from further translating. For illustration purposes only, the sliding element 740 of the intervertebral device 700 may be translated through the use of a tool, such as exemplary tool 600 described above with respect to intervertebral device 500, the distal portion of the sliding element 740 including protrusions and grooves to interface with the tool 600, for example.

Figure 34:
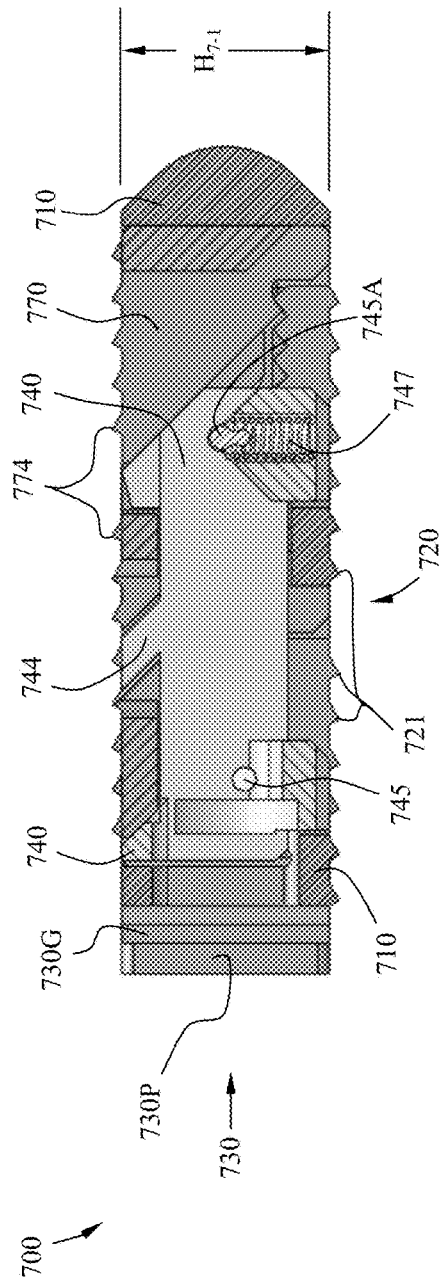
FIG. 34 is a partial section view of another exemplary intervertebral device.
Figure 35:
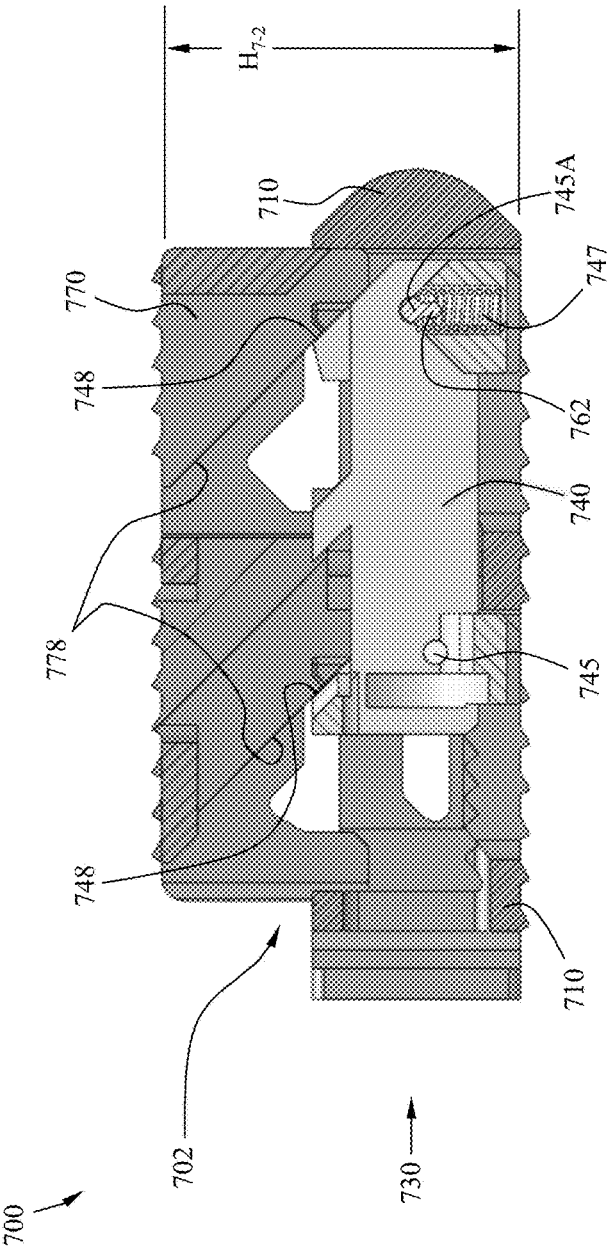
FIG. 35 is another partial section view of the exemplary intervertebral device of FIG. 34.

Turning to FIGS. 34 and 35, the intervertebral device 700 is depicted in cross-section along section A-A of FIG. 31. The intervertebral device 700 is depicted in a collapsed configuration in FIG. 34 and an expanded configuration in FIG. 35. In particular, the sliding element 740 includes a device 760 to aide in maintaining contact between the engaging element 750, 736 of the sliding element 740 and base element 710, respectively. The retention device 760 includes the pin 745A and spring 747, the spring 747 seated in bore 748. As depicted, the pin 745A may extend from a first opening 723 in side portion 716 to a second opening 723 in side portion 718 (not shown), similar to openings 128 of the intervertebral device of FIG. 1. The pin 745A includes a protrusion 762 that extends from a central longitudinal axis of the pin 745A toward the bottom 720 of the first element 710. In operation, as the sliding element 740 translates between the two ends 712, 714, the engaging elements 750, 736 repeatedly engage and disengage resulting in the sliding element 740 repeatedly moving vertically away from and toward to the bottom portion 720 of the base element 710, as described above with respect to the intervertebral device 500. As the sliding element 740 moves away from the base element 710 the ends of the pin 745A engage the top surfaces of the corresponding openings 723 in respective side portions 716, 718, acting to compress the spring 747. As the engaging elements 750 of the sliding element 740 pass over the corresponding engaging elements 736 of the base element 710 the spring imparts a force upon the sliding element 740 to encourage re-engagement of the adjacent engaging elements 750, 736. In this way, the engaging elements 750 are biased to remain coupled to corresponding engaging elements 736 during each movement of the sliding element 740, particularly in a no-load situation, where the force between the third element 770 and the first element 710 is minimal for examples. Accordingly, when a compression force is applied between the top surface 771 of the third element 770 and the bottom surface 720 of the base element 710, engaging elements 750, 736 maintain the current position of all three element 710, 740, 770 and, ultimately, the current height, $H_7$, of the intervertebral device 700.

Figure 36:
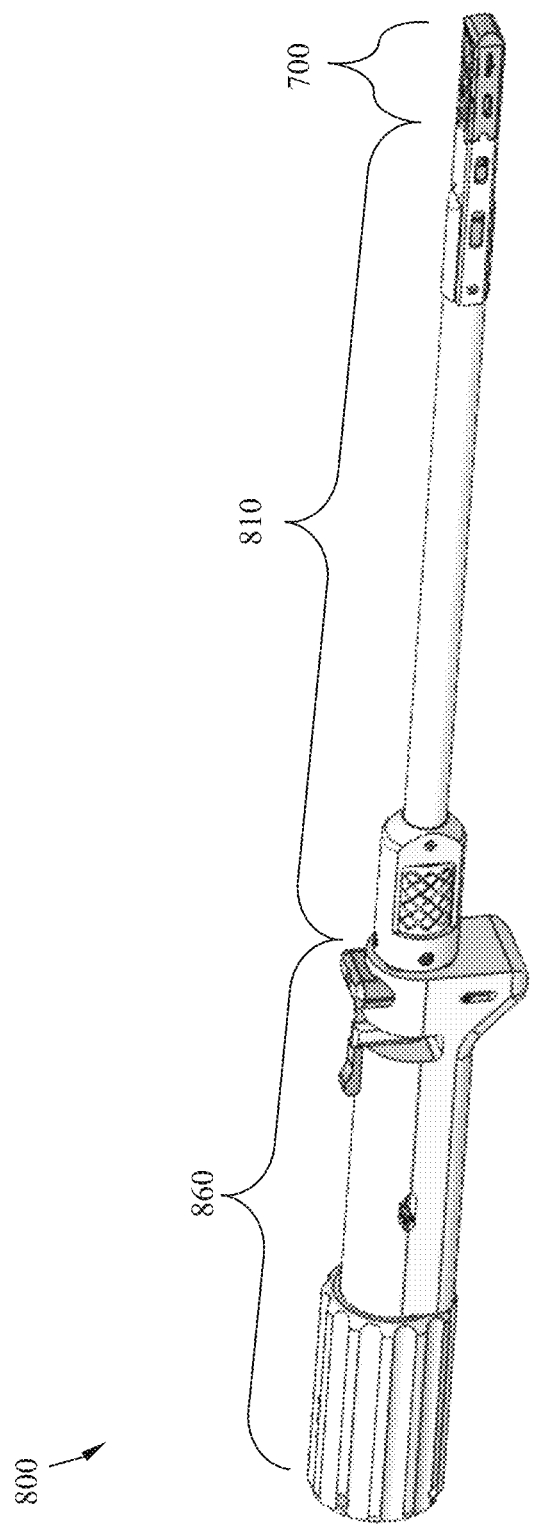
FIG. 36 is a perspective view of another exemplary delivery device.
Figure 37:
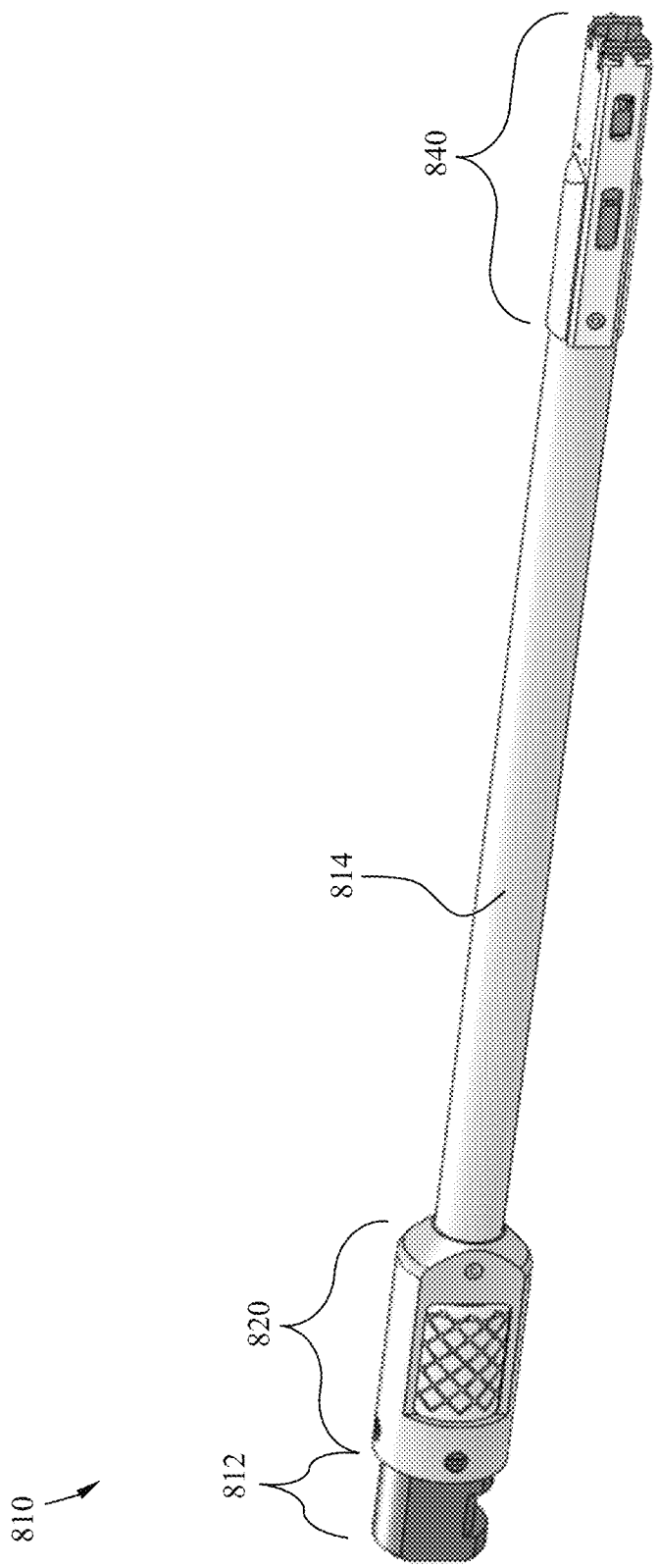
FIG. 37 is a perspective view of a portion of the exemplary delivery device of FIG. 36.

Turning to FIG. 36, a delivery system 800 for positioning and operating intervertebral device 700, or other intervertebral devices described or contemplated herein, includes an attachment assembly 810 and an expansion tool 860. The attachment assembly 810 is utilized for attaching the intervertebral device, such as intervertebral device 700, to the delivery system 800. The expansion tool 860 is utilized for setting a height of the intervertebral device 700 once the device 700 has been deployed, between adjacent vertebrae for example. Turning to FIG. 37, the attachment assembly 810 includes an interface unit 812, a control assembly 820, a grasper unit 840, and an elongate member 814 that extends from the control assembly 820 to the grasper unit 840. The interface unit 812 is configured to attach the attachment assembly 810 to the expansion tool 860, as is discussed in greater detail below. The elongate member 814 may include one or more lumens or members therein for controlling the grasper unit 840 or the intervertebral device 700.

Figure 38:
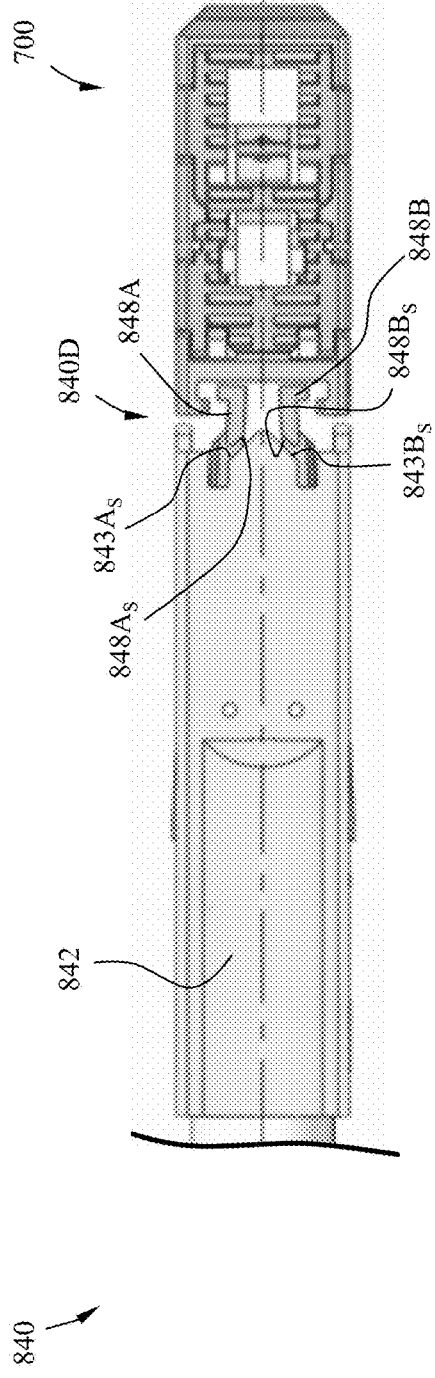
FIG. 38 is a top view of an element of the portion of the exemplary intervertebral device of FIG. 37.

Turning to FIGS. 38-41, operation of the grasper unit 840 will be described in greater detail. The grasper unit 840 includes a housing 842 having first and second slots $842_{S1}$, $842_{S2}$, a control ring 844 operational coupled to first and second arms 846A, 846B. The elongate member 814 is fixedly coupled to the housing 842 via pins 815. An elongate member 816 passes through a lumen of the elongate member 814, and includes a threaded portion 816T that is rotationally coupled to threaded portion 844T of the control ring 844. Rotational movement of the elongate member 816 is transformed into axial movement of the control ring 844 through treaded portions 816T, 844T. First arm 846A includes first and second protrusions $846A_{P1}$, $846A_{P2}$ positioned within slots $842A_{S1}$, $842A_{S2}$, respectively, and a third protrusion $846A_{P3}$ at a distal tip of the arm 846A. Similarly, second arm 846B includes first and second protrusions $846B_{P1}$, $846B_{P2}$ positioned within slots $842B_{S1}$, $842B_{S2}$, respectively, and a third protrusion $846B_{P3}$ at a distal tip of the arm 846B. As depicted in FIG. 38, arm 846A includes a raised portion 848A configured to engage a surface of housing 842. More specifically, the raised portion 848A includes a surface $848A_S$ configured to engage a surface $843A_S$ of the housing. In similar fashion, arm 846B includes a raised portion 848B having a surface $848A_S$ configured to engage a surface $843A_S$ of the housing. Accordingly, as the housing 842 moves distally relative to the arms 846A, 846B, a distance between the protrusions $846A_{P3}$, $846B_{P3}$ increases.

Figure 39:
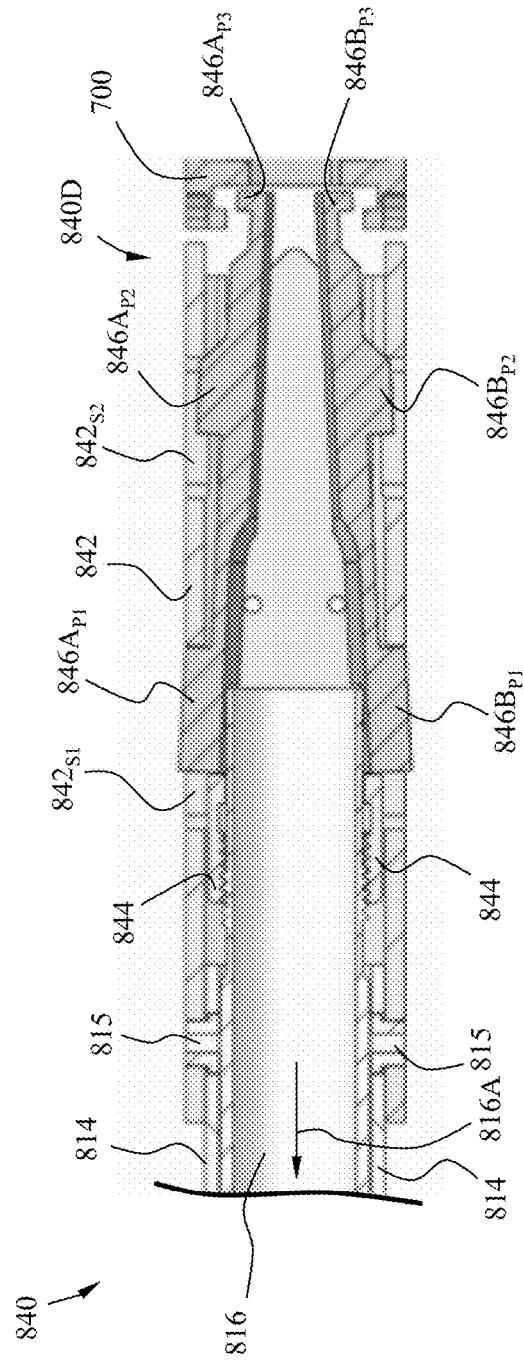
FIG. 39 is a partial section view of the element of the portion of the exemplary intervertebral device of FIG. 37.
Figure 40:
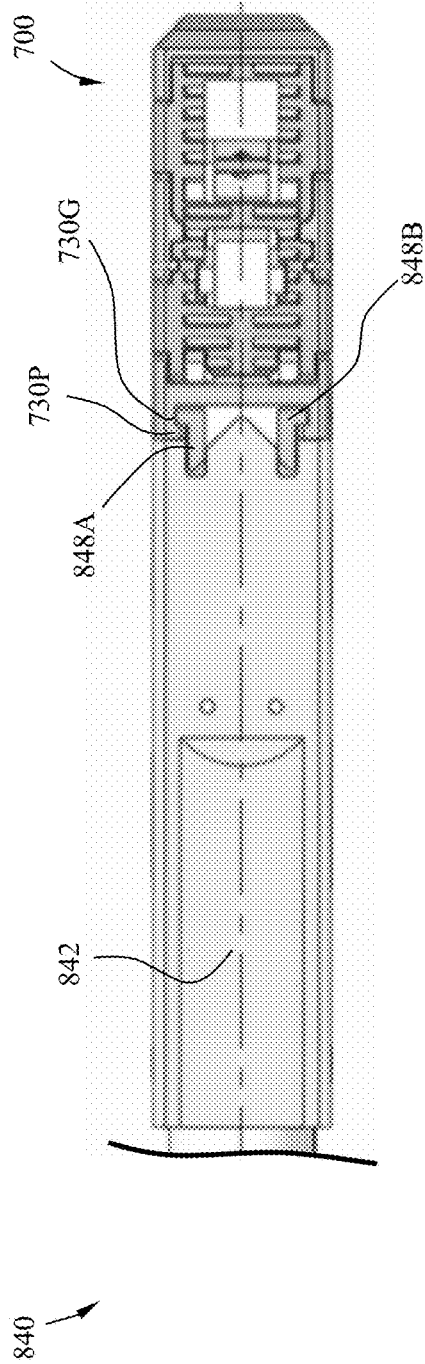
FIG. 40 is another top view of an element of the portion of the exemplary intervertebral device of FIG. 37.
Figure 41:
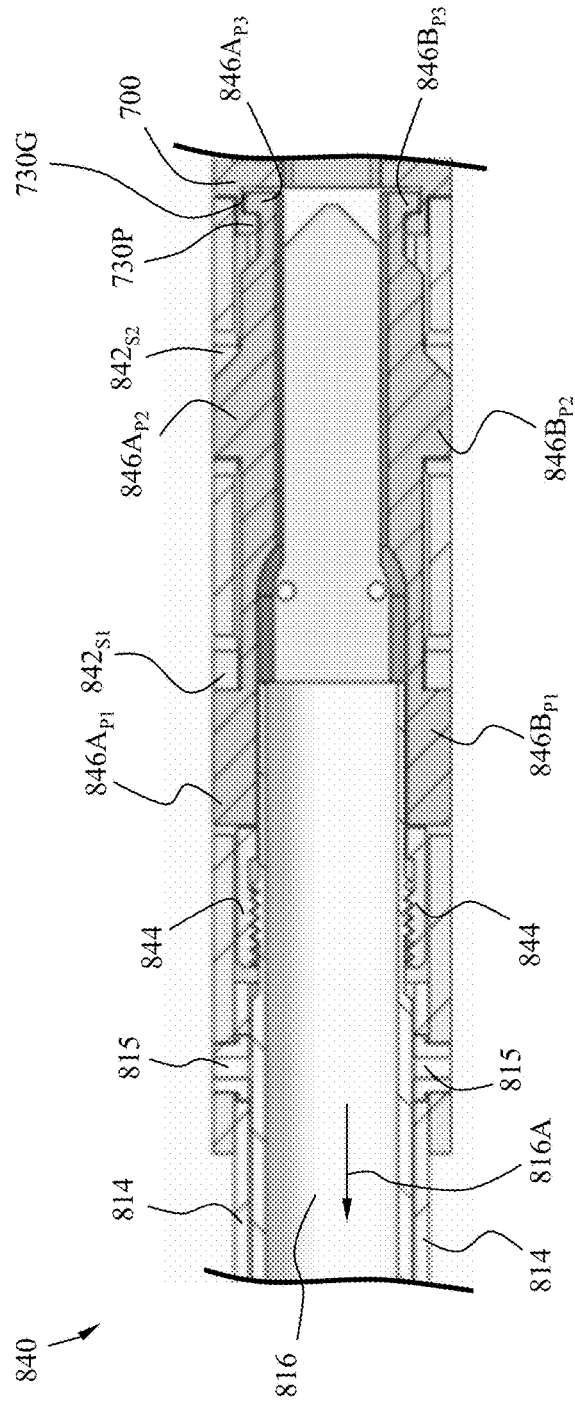
FIG. 41 is another partial section view of the element of the portion of the exemplary intervertebral device of FIG. 37.

FIGS. 38 and 39 depict the arms 846A, 846B in an open configuration, while FIGS. 40 and 41 depict the arms 846A, 846B in a closed configuration, the arms 846A, 846B being closer to each other in the open configuration than in the closed configuration. In operation, rotation of the elongate member 816 in a first direction results in axial movement of the control ring 844 as indicated by arrow 816A. Since the control ring 844 is coupled to the arms 846A, 846B, the arms move in the same direction as the control ring, and the surfaces $848A_S$, $848B_S$ cooperate with surfaces $843A_S$, $843B_S$ of housing 842 to move the arms apart from each other, e.g., transitioning to a closed configuration for example. Continued axial movement of the control ring results in moving the arms 846A, 846B axially to clamp onto the proximal features 730PA and 730PB. Rotation of the elongate member 816 in a second direction opposite to the first direction, results in axial movement of the control ring 844 in a direction opposite to that indicated by arrow 816A. As the control ring 844 moves distally with respect to housing 842, as well as arms 846A, 846B, distal surfaces of protrusions $846A_{P3}$, $846B_{P2}$ engage or cooperate with distal portions of slots $842_{S2}$ to deflect the arms inward. Accordingly, the more the arms 846A, 846B move distally with respect to the housing 842, the more the distal protrusions 846AP3, 846BP3 move distally and toward to each other, disengaging from the attachment point, and being free from the profile of the protrusions 730PA and 730PB, of the intervertebral device 700.

Turning to FIGS. 42A-42C, the interaction between the control ring 844, arms 846A, 846B, and the elongate member 816 is depicted. The control ring 844 includes first and second "T" slots 845, each coupled to a proximal end of one of the arms 846A, 846B, as depicted in FIG. 42B. The coupling point between the slots 845 and the arms 846A, 846B allows for the distal protrusions $846A_{P3}$, $846B_{P3}$ to move toward and away from each other to enable a position for coupling between the arms 846A, 846B and the intervertebral device 700. FIG. 42C depicts the control ring 844 rotatably coupled to the elongate tube 816.

Figure 43:
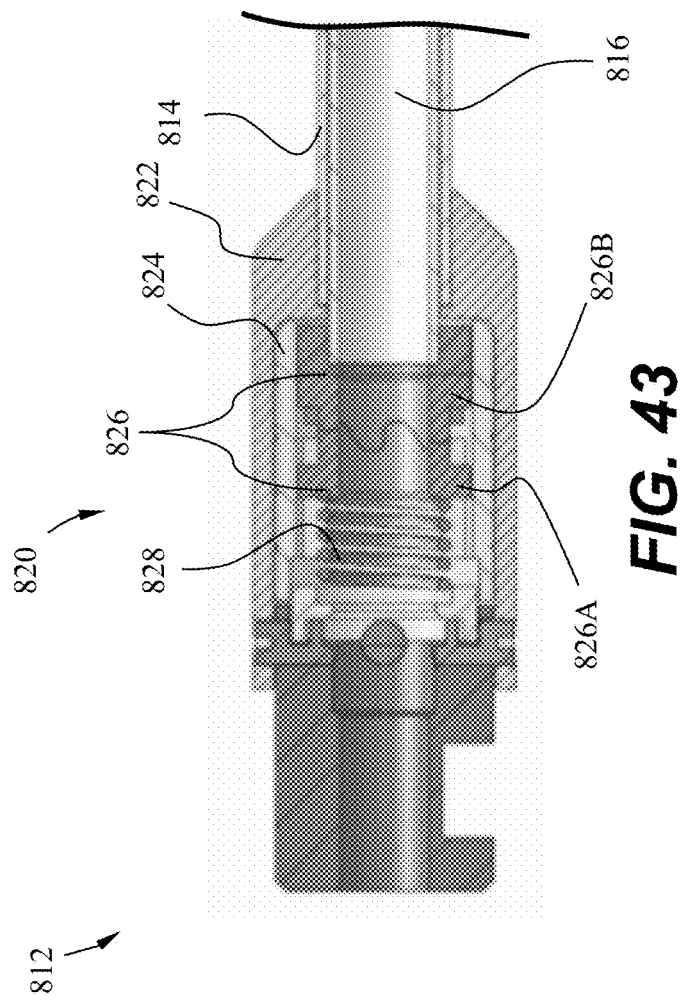
FIG. 43 is a partial section view of a portion of the exemplary delivery device of FIG. 36.

Turning to FIG. 43, the interface unit 812 is fixedly attached to the control assembly 820, the control assembly 820 fixedly attached to elongate member 814. The control assembly 820 includes a rotatable control 824, a clutch assembly 826, and a spring 828. The rotatable control 824 is rotationally attached to a clutch member 826A, as part of a clutch assembly 826. A clutch member 826B is rotationally attached to elongate member 816. The spring 828 provides a force to encourage coupling between clutch member 826A and clutch member 826B at fingers 826F. The fingers are configured such that rotation of the rotatable control 824 in a first direction results in constant engagement of the fingers, and rotation of the rotatable control 824 in a second direction opposite to the first direction results in the fingers of clutch member 826A slipping past the fingers of clutch member 826B once the rotational torque becomes greater than the force applied by the spring 826 on the clutch member 826A. In this way, rotation of the rotatable control 824 in the second direction results in the arms 846A, 846B couplings to the attachment point of the intervertebral device 700, without over-tightening the connection which may result in undue stress in the delivery system 800 or the intervertebral device 700, or both.

Figure 44:
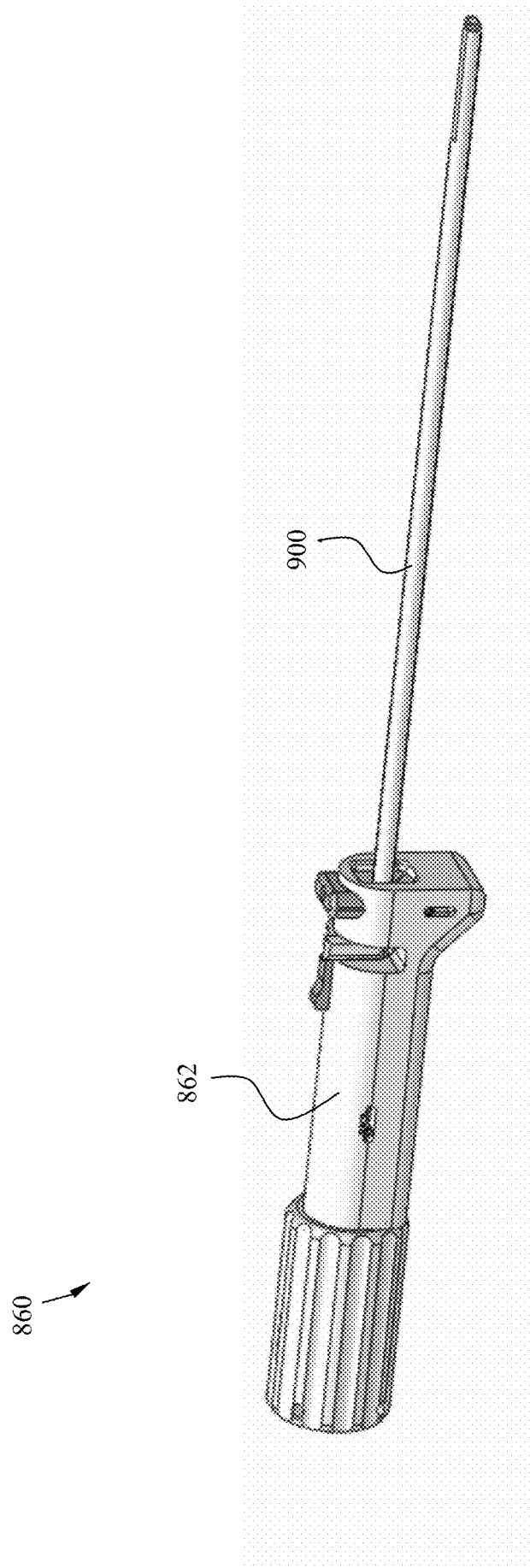
FIG. 44 is a perspective view of an element of the exemplary delivery device of FIG. 36.

Turning to FIG. 44, the expansion tool 860 includes a handle or handle portion 862 and an elongate shaft rotatably coupled to the handle 862. The expansion tool 860 is utilized for moving the second element, for example the second element 730 of the intervertebral device 700, along a longitudinal axis of the first element 710 to set a height of the intervertebral device 700 once the device 700 has been deployed, between adjacent vertebrae for example.

Figure 45A:
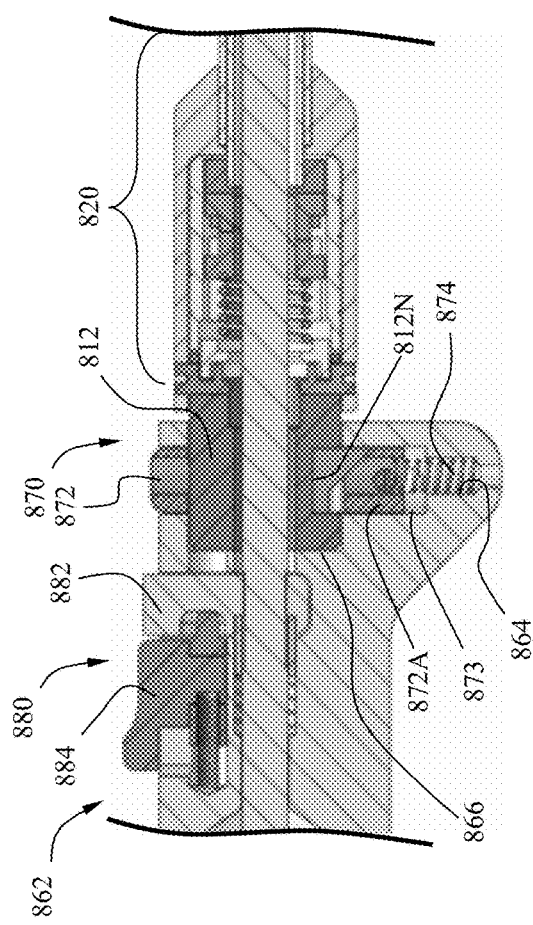
FIGS. 45A-45B are partial section views of portions of the delivery device of FIG. 33
Figure 45B:
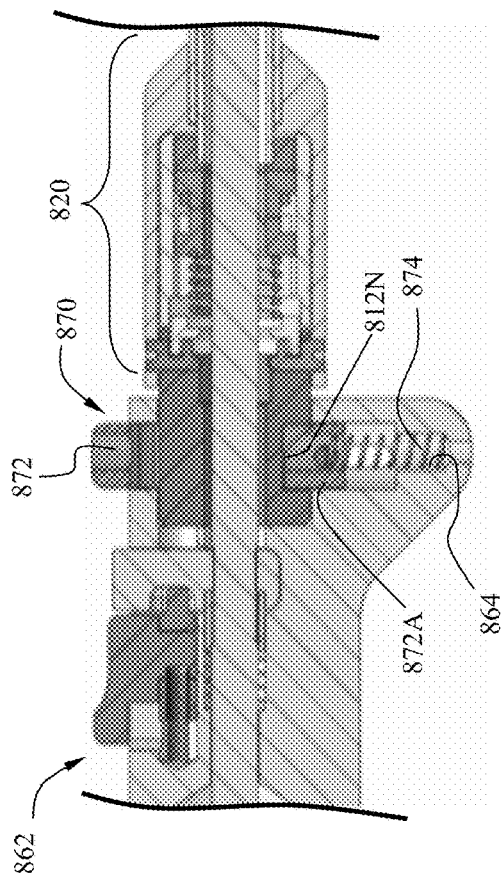

Turning to FIGS. 45A and 45B, handle portion 862 includes an interface assembly 870 and an attachment control 880. The interface assembly 870 is configured to attach or interface the handle portion 862 with the attachment assembly 810. More specifically, the interface assembly 870 interfaces with the interface element 812 of the attachment assembly 810. The interface assembly 870 includes a pushbutton 872 in a slotted portion 873 of the handle 862. The pushbutton 872 is biased by a spring 874, which is positioned within a bore 864 of the handle 862. With specific reference to FIG. 45A, when the pushbutton 872 is depressed, compressing the spring 874, the interface element 812 of the attachment assembly 810 may be positioned within an opening 866 within the handle 862. The interface element 812 includes a notch 812N sized to be equal to or greater than a width of the pushbutton 872, such that once the interface element 812 is positioned within the opening 866 the pushbutton 872 may be released and a portion 872A of the pushbutton 872 is positioned within the notch 812N, as depicted in FIG. 45B.

Attachment control 880 is utilized to engage the second element, for example element 730, with the elongate shaft 900. The control 880 includes a lever 882 rotatably coupled to the shaft 900, the lever 882 being configured to rotate the shaft to enable engagement of the shaft 900 with the second element 740. The control 880 may further include a slide lock 884, which is configured to lock the lever control 882 such that the shaft 900 is maintained in a desired rotational orientation, during operation of an intervertebral device for example.

Turning to FIGS. 46A and 46B, a distal end 902 of elongate shaft 900 includes a protrusion 904 adjacent to a groove 906. The protrusion 904 may be adapted to fit a corresponding groove 740G at a proximal end of the sliding element 740. As depicted in FIG. 46A, the shaft 900 is angled or rotated along its axis such that the protrusion 904 freely enters the proximal end of the sliding element 740. Once inserted, the shaft 900 may be rotated, through operation of the attachment control 880 for example, such that the protrusion 904 is positioned within the groove 740G and held in place through the cooperation of the protrusion 904 and a protrusion 740P at the proximal end of sliding or third element 740, as depicted in FIG. 46B.

The groove 740G of the sliding element 740 cooperates with the protrusion 904 of the shaft 900 to rigidly attach the shaft 900 to the element 740. Once the shaft 900 is rigidly attached to the sliding element 740 a user can translate the sliding element 740 through corresponding translation of the shaft. Turning to FIGS. 47 and 48, the handle 862 may also include an axial control 890 configured to translate the shaft 900 in proximal and distal directions. The axial control 890 includes a rotational control 892 having threaded portion 894 that interfaces with corresponding threaded portion 862T of the handle 862, the axial control 890 being coupled to the shaft 900. Shaft 900 is axially coupled, not rotationally coupled, to the rotational control 892. Accordingly, the axial control 890 converts rotational movement of the control 892 into axial movement of the shaft 900. As the rotational control 892 is rotated in a first direction the control 892 moves distally within the handle portion, which acts to move shaft 900 distally. As the rotational control 892 is rotated in a second direction the control 892 moves proximally within the handle portion, which acts to move shaft 900 proximally. Translation of the shaft 900 results in the translation of the sliding element 740, further resulting in the sliding element 740 moving between the ends 712, 714 of the base member 710. As the sliding element 740 translates or moves between the ends 712, 714, the element 770 moves in a vertical direction with respect to the base element 710 to change the overall height, H, of the intervertebral device 700.

The intervertebral devices described herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding). The intervertebral devices herein may be sized for minimally invasive procedures having operating lumens at about 12 mm or less.

It should be understood that features of any one of the above-described intervertebral devices described herein may be applied to any other of the above-described intervertebral devices, as appropriate. The intervertebral devices described herein may be made from any suitable biocompatible material, including but not limited to metals, metal alloys (e.g. stainless steel) and polymers (e.g., polycarbonate), and may be formed using any appropriate process, such as screw-machining or molding (e.g., injection molding). The intervertebral devices herein may be sized for minimally invasive procedures having operating lumens at about 12 mm or less.

What is claimed is:

1. A device, comprising:
   a base including a first end and a second end, and a bottom surface configured to interface with a first biological tissue;
   a first body portion slidably attached to the base and configured to move in at least a first direction with respect to the base, the first body portion including a first plurality of engaging elements,
   a second body portion slidably attached to the base and configured to move in at least a second direction with respect to the base, the second body portion including a top surface configured to interface with a second biological tissue,
   the base including a second plurality of engaging elements, at least one of the first plurality of engaging elements being configured to engage and disengage with adjacent opposing ones of the second plurality of engaging elements as the first body portion moves in the first direction,
   the first body portion including a first pair of sloped surfaces and a second pair of sloped surfaces, each of the first and second pairs of sloped surfaces being substantially parallel to a remaining one of the first and second pairs of sloped surfaces,
   the base being configured to limit movement of the first body portion to movement between the first and second ends of the base.

2. The device of claim 1, wherein the first and second pluralities of engaging elements are configured to prevent movement of the second body portion in a third direction with respect to the base when a compression force is applied between the top surface of the second body portion and the bottom surface of the base.

3. The device of claim 2, wherein the third direction is substantially opposite to the first direction.

4. The device of claim 1, wherein the second direction is substantially orthogonal to the first direction.

5. The device of claim 1, wherein the second body portion includes a third pair of sloped surfaces and a fourth pair of sloped surfaces, the first pair of sloped surfaces of the first body portion being configured to slidably couple with the third pair of sloped surfaces of the second body portion and the second pair of sloped surfaces of the first body portion being configured to slidably couple with the fourth pair of surfaces of the second body portion, such that movement of the first body portion in the first direction results in movement of the second body portion in the second direction.

6. The device of claim 5, wherein the first pair of sloped surfaces of the first body portion forms a first acute angle with respect to a longitudinal axis of the base, the second pair of sloped surfaces of the first body portion forms a second acute angle with respect to the longitudinal axis of the base, the first acute angle being substantially equal to the second acute angle.

7. The device of claim 5, wherein the first pair of sloped surfaces of the first body portion forms a first acute angle with respect to a longitudinal axis of the base, the second pair of sloped surfaces of the first body portion forms a second acute angle with respect to the longitudinal axis of the base, movement of the second body portion relative to the first body portion having a movement rate, the first and second acute angles being selected to provide the movement rate.

8. The device of claim 1, wherein the first body portion is configured to be removably attached to a tool, the tool configured to move the first body portion along a longitudinal axis of the base.

9. The device of claim 1, wherein the base includes a longitudinal axis, the first direction being substantially parallel to the longitudinal axis of the base.

10. The device of claim 1, wherein the base includes a longitudinal axis, the second direction being substantially perpendicular to the longitudinal axis of the base.

11. The device of claim 1, wherein the first direction and the second direction are substantially perpendicular.

12. The device of claim 1, wherein the base includes a longitudinal axis extending from the first end to the second end, each of a plurality of positions of the first body portion along the longitudinal axis of the base corresponding to a respective one of a plurality of positions of the second body portion.

13. The device of claim 12, wherein each of the plurality of positions of the first body portion corresponds to a respective one of a plurality of heights of the device.

14. The device of claim 1, wherein the first direction is in a direction toward a distal end of the device along a longitudinal axis of the base.

15. The device of claim 1, wherein the first direction is in a direction toward a proximal end of the device along a longitudinal axis of the base.

16. The device of claim 1, wherein the first plurality of engaging elements are located along a bottom surface of the first body portion.

* * * * *